US011854123B2

(12) United States Patent
Bai et al.

(10) Patent No.: US 11,854,123 B2
(45) Date of Patent: Dec. 26, 2023

(54) SPARSE BACKGROUND MEASUREMENT AND CORRECTION FOR IMPROVING IMAGING

(71) Applicant: Accuray, Inc., Sunnyvale, CA (US)

(72) Inventors: Chuanyong Bai, Solon, OH (US); Robert Zahn, Chagrin Falls, OH (US); Daniel Gagnon, Twinsburg, OH (US); Amit Jain, Solon, OH (US); Zhicong Yu, Highland Hts., OH (US); Georgios Prekas, Solon, OH (US)

(73) Assignee: Accuray, Inc., Sunnyvale, CA (US)

( * ) Notice: Subject to any disclaimer, the term of this patent is extended or adjusted under 35 U.S.C. 154(b) by 28 days.

(21) Appl. No.: 17/383,740

(22) Filed: Jul. 23, 2021

(65) Prior Publication Data
US 2023/0026441 A1 Jan. 26, 2023

(51) Int. Cl.
*G06T 11/00* (2006.01)
*A61B 6/00* (2006.01)
(Continued)

(52) U.S. Cl.
CPC ............ *G06T 11/005* (2013.01); *A61B 6/027* (2013.01); *A61B 6/032* (2013.01); *A61B 6/4085* (2013.01);
(Continued)

(58) Field of Classification Search
CPC . G06T 11/005; G06T 2211/408; A61B 6/027; A61B 6/032; A61B 6/4085;
(Continued)

(56) References Cited

U.S. PATENT DOCUMENTS

| 4,190,773 A | 2/1980 | Braden et al. |
| 5,615,279 A | 3/1997 | Yoshioka et al. |

(Continued)

FOREIGN PATENT DOCUMENTS

| DE | 102006007058 A1 | 7/2007 |
| DE | 102012200150 A1 | 7/2013 |

(Continued)

OTHER PUBLICATIONS

Anas, et al., High-quality 3D correction of ring and radiant artifacts in flat panel detector-based cone beam volume CT imaging, Phys. Med. Biol., 2011, pp. 6495-6519, vol. 56.

(Continued)

*Primary Examiner* — Courtney D Thomas
(74) *Attorney, Agent, or Firm* — Calfee, Halter & Griswold LLP

(57) ABSTRACT

Disclosed herein is an imaging system including a first x-ray source configured to produce first x-ray photons in a first energy range suitable for imaging, project the first x-ray photons onto an area designated for imaging, a rotatable gantry configured to rotate the first x-ray source such that the first x-ray source traverses an angular path, and a data processor having an analytical portion. The analytical portion is configured to collect first data relating to the transmission of the first x-ray photons through the area designated for imaging at a set of image-collection angles along the angular path, collect background data at a set of background-collection angles along the angular path, wherein the system acquires more than one image of the designated area for imaging between background angles. The analytical portion is also configured to remove errors in the first data using the background data, and generate a corrected image based on the removal of errors in the first data.

38 Claims, 11 Drawing Sheets

(51) Int. Cl.
*A61B 6/02* (2006.01)
*A61B 6/03* (2006.01)

(52) U.S. Cl.
CPC .............. *A61B 6/4435* (2013.01); *A61B 6/54* (2013.01); *G06T 2211/408* (2013.01)

(58) Field of Classification Search
CPC ....... A61B 6/4435; A61B 6/54; A61B 6/4014; A61B 6/482
See application file for complete search history.

(56) References Cited

U.S. PATENT DOCUMENTS

| | | | |
|---|---|---|---|
| 6,233,478 | B1 | 5/2001 | Liu |
| 6,307,909 | B1 | 10/2001 | Flohr et al. |
| 7,050,528 | B2 | 5/2006 | Chen |
| 7,108,421 | B2 | 9/2006 | Gregerson et al. |
| 7,302,038 | B2 | 11/2007 | Mackie et al. |
| 7,336,759 | B2 | 2/2008 | Nukui |
| 7,433,443 | B1 | 10/2008 | Tkaczyk et al. |
| 7,660,380 | B2 | 2/2010 | Boese et al. |
| 8,116,430 | B1 | 2/2012 | Shapiro et al. |
| 8,467,497 | B2 | 6/2013 | Lu et al. |
| 8,588,363 | B2 | 11/2013 | Flohr |
| 9,400,332 | B2 | 7/2016 | Star-Lack et al. |
| 9,952,164 | B2 | 4/2018 | Wiedmann et al. |
| 11,337,668 | B2 | 5/2022 | Yu et al. |
| 2003/0007601 | A1 | 1/2003 | Jaffray et al. |
| 2003/0076927 | A1 | 4/2003 | Nakashima et al. |
| 2004/0068169 | A1 | 4/2004 | Mansfield et al. |
| 2004/0091079 | A1 | 5/2004 | Zapalac |
| 2004/0202360 | A1 | 10/2004 | Besson |
| 2005/0053188 | A1 | 3/2005 | Gohno |
| 2005/0251029 | A1 | 11/2005 | Khamene et al. |
| 2006/0104496 | A1 | 5/2006 | Arenson et al. |
| 2006/0109954 | A1 | 5/2006 | Gohno |
| 2006/0262894 | A1 | 11/2006 | Bernhardt et al. |
| 2007/0127621 | A1 | 6/2007 | Grass et al. |
| 2007/0189444 | A1 | 8/2007 | Van Steven-Daal et al. |
| 2007/0237288 | A1 | 10/2007 | Tkaczyk et al. |
| 2008/0103834 | A1 | 5/2008 | Reiner |
| 2008/0112532 | A1 | 5/2008 | Schlomka |
| 2009/0080603 | A1 | 3/2009 | Shukla et al. |
| 2009/0135994 | A1 | 5/2009 | Yu et al. |
| 2009/0161826 | A1 | 6/2009 | Gertner et al. |
| 2009/0225932 | A1 | 9/2009 | Zhu et al. |
| 2009/0283682 | A1 | 11/2009 | Star-Lack et al. |
| 2009/0304142 | A1 | 12/2009 | Ruimi et al. |
| 2010/0046819 | A1 | 2/2010 | Noo et al. |
| 2010/0142791 | A1 | 6/2010 | Tsuji |
| 2010/0208964 | A1 | 8/2010 | Wiegert et al. |
| 2011/0060566 | A1 | 3/2011 | Bertram et al. |
| 2011/0142312 | A1 | 6/2011 | Toth et al. |
| 2011/0176717 | A1 | 7/2011 | Siren et al. |
| 2011/0255656 | A1 | 10/2011 | Star-Lack et al. |
| 2011/0255657 | A1 | 10/2011 | Noordhoek |
| 2012/0014582 | A1 | 1/2012 | Schaefer et al. |
| 2012/0121157 | A1* | 5/2012 | Irie .................. A61B 6/503 382/131 |
| 2012/0207370 | A1 | 8/2012 | Fahimian et al. |
| 2012/0263360 | A1 | 10/2012 | Zhu et al. |
| 2012/0294504 | A1 | 11/2012 | Kyriakou |
| 2013/0004052 | A1* | 1/2013 | Chen .................. G06T 7/251 382/132 |
| 2013/0101082 | A1 | 4/2013 | Jordan et al. |
| 2013/0294570 | A1 | 11/2013 | Hansis |
| 2014/0018671 | A1 | 1/2014 | Li et al. |
| 2014/0086383 | A1 | 3/2014 | Huwer et al. |
| 2014/0105352 | A1 | 4/2014 | Williams |
| 2014/0110594 | A1 | 4/2014 | Star-Lack et al. |
| 2014/0169652 | A1 | 6/2014 | Vic et al. |
| 2015/0297165 | A1 | 10/2015 | Tanaka et al. |
| 2015/0305696 | A1 | 10/2015 | Yamakawa et al. |
| 2016/0005194 | A1 | 1/2016 | Schretter et al. |
| 2016/0016009 | A1 | 1/2016 | Manzke et al. |
| 2016/0120486 | A1 | 5/2016 | Goto et al. |
| 2016/0220844 | A1 | 8/2016 | Paysan et al. |
| 2016/0262709 | A1 | 9/2016 | Siewerdsen et al. |
| 2017/0000428 | A1 | 1/2017 | Goto |
| 2017/0197098 | A1 | 7/2017 | Hirasawa et al. |
| 2017/0205360 | A1 | 7/2017 | Cinquin et al. |
| 2017/0278277 | A1 | 9/2017 | Morf et al. |
| 2017/0332982 | A1 | 11/2017 | Koehler et al. |
| 2018/0028143 | A1 | 2/2018 | Wiggers et al. |
| 2018/0070894 | A1 | 3/2018 | Osaki et al. |
| 2018/0144510 | A1 | 5/2018 | Lachaine |
| 2018/0192978 | A1 | 7/2018 | Naylor et al. |
| 2018/0345042 | A1 | 12/2018 | Voronenko et al. |
| 2019/0099149 | A1 | 4/2019 | Li |
| 2020/0016432 | A1 | 1/2020 | Maolinbay |
| 2020/0121267 | A1 | 4/2020 | Deutschmann |
| 2020/0402644 | A1 | 12/2020 | Zhou et al. |
| 2021/0165122 | A1 | 6/2021 | Morton |

FOREIGN PATENT DOCUMENTS

| | | |
|---|---|---|
| EP | 1062914 A1 | 12/2000 |
| EP | 2383702 A1 | 11/2011 |
| JP | H08252248 A | 10/1996 |
| JP | 09218939 A | 8/1997 |
| JP | H105210 A | 1/1998 |
| JP | 2004000356 A | 1/2004 |
| JP | 2004136021 A | 5/2004 |
| JP | 2005080919 A | 5/2004 |
| JP | 2004223255 A | 8/2004 |
| JP | 2004530467 A | 10/2004 |
| JP | 2006141999 A | 6/2006 |
| JP | 2006239003 A | 9/2006 |
| JP | 2008036275 A | 2/2008 |
| JP | 2008544831 A | 12/2008 |
| JP | 2009533086 A | 9/2009 |
| JP | 2009297314 A | 12/2009 |
| JP | 2010284325 A | 12/2010 |
| JP | 2011067555 A | 4/2011 |
| JP | 2012024145 A | 2/2012 |
| JP | 2014511186 A | 5/2014 |
| JP | 2014528767 A | 10/2014 |
| JP | 2017131496 A | 8/2017 |
| JP | 2017185219 A | 10/2017 |
| JP | 2017531228 A | 10/2017 |
| WO | 2005112753 A2 | 12/2005 |
| WO | 2006078386 A2 | 7/2006 |
| WO | 2010014288 A1 | 2/2010 |
| WO | 2010099621 A1 | 9/2010 |
| WO | 2015103184 A1 | 7/2015 |
| WO | 2017104700 A1 | 6/2017 |
| WO | 2018156968 A1 | 8/2018 |
| WO | 2018183748 A1 | 10/2018 |

OTHER PUBLICATIONS

Bootsma, et al., Spatial frequency spectrum of the x-ray scatter distribution in CBCT projections, Med. Phys., Nov. 2013, pp. 111901-1-111901-15, vol. 40, No. 11.
International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correction methods in cone beam CT. Part 2: Scatter estimation approaches, Med. Phys. Sep. 2011, pp. 5186-5199, vol. 38, No. 9.
Yang, et al., Scattering estimation for cone-Beam CT Using Local Measurement Based on Compressed Sensing, IEEE transactions on Nuclear Science, Mar. 2018, pp. 941-949, vol. 65, No. 3.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.

(56) References Cited

OTHER PUBLICATIONS

Hsieh, et al., A novel reconstruction algorithm to extend the CT scan field-of-view, Med. Phys., Sep. 2004, pp. 2385-2391, vol. 31, No. 9.
International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063074 dated Mar. 23, 2020.
International Search Report and Written Opinion from PCT/US2019/063076 dated Mar. 16, 2020.
International Search Report and Written Opinion from PCT/US2019/063077 dated Mar. 16, 2020.
International Search Report and Written Opinion from PCT/US2019/063078 dated Oct. 8, 2020.
International Search Report and Written Opinion from PCT/US2019/063080 dated Mar. 16, 2020.
International Search Report and Written Opinion from PCT/US2019/063083 dated Mar. 16, 2020.
International Search Report and Written Opinion from PCT/US2019/063085 dated Mar. 16, 2020.
International Search Report and Written Opinion from PCT/US2019/063086 dated Nov. 16, 2020.
International Search Report and Written Opinion from PCT/US2019/063087 dated Apr. 3, 2020.
Invitation to Pay Additional Fees from PCT/US2019/063086 dated Mar. 26, 2020.
Kang, et al., Accurate positioning for head and neck cancer patients using 2D and 3D image guidance, Journal of Applied Clinical Medical Physics, Mar. 2011, pp. 1-14, vol. 12, No. 1.
Katsevich, A., An improved exact filtered backprojection algorithm for spiral computed tomography, Advances in Applied Mathematics, 2004, pp. 691-697, vol. 32.
Kudo, et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li, et al., Scatter kernel estimation with an edge-spread function method for cone-beam computed tomography imaging, Physics in Medicine and Biology, pp. 6729-6748, vol. 51.
Lindsay, et al., Investigation of combined kV/MV CBCT imaging with a high-DQE MV detector, Med. Phys., Feb. 2019, pp. 563-575, vol. 46, No. 2.
Liu, et al., X-Ray micro-CT with a displaced detector array: Application to helical cone-beam reconstruction, Medical Physics, Oct. 2003, pp. 2758-2761, vol. 30, No. 10.
Maslowski, et al., Acuros CTS: A fast, linear Boltzmann transport equation solver for computed tomography scatter-Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo, et al., A new scheme for view-dependent data differentiation in fan-beam and cone-beam computed tomography, Physics in Medicine and Biology, 2007, pp. 5593-5414, vol. 52.
Notice of Allowance from U.S. Appl. No. 16/694,190 dated Jun. 23, 2021, 8 pages.
Office Action from U.S. Appl. No. 16/694,202 dated Apr. 9, 2021, 12 pages.
Office Action from U.S. Appl. No. 16/694,145 dated Mar. 17, 2021, 10 pages.
Office Action from U.S. Appl. No. 16/694,190 dated Mar. 26, 2021, 9 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Office Action from U.S. Appl. No. 16/694,161 dated Sep. 13, 2021, 18 pages.
Office Action from U.S. Appl. No. 16/694,230 dated Apr. 1, 2021, 6 pages.
Ramamurthi, et al., Region of Interest Cone Beam Tomography With Prior CT Data, Conference Record of the 37th Asilomar Conference on Signals, Systems, & Computers, Nov. 2003, pp. 1924-1927, vol. 2.
Restriction Requirement from U.S. Appl. No. 16/694,210 dated Jun. 10, 2021, 6 pages.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Schäfer, et al., FBP and BPF reconstruction methods for circular X-ray tomography with off-center detector, Med. Phys., Jul. 2011, pp. S85-S94, vol. 38, No. 7.
Siewerdsen, et al., A simple, direct method for x-ray scatter estimation and correction in digital radiography and cone-beam CT, Med. Phys., Jan. 2006, pp. 187-197, vol. 33, No. 1.
Spearman, et al., Effect of Automated Attenuation-based Tube Voltage Selection on Radiation Dose at CT: An Observational Study on a Global Scale, Radiology, Apr. 2016, pp. 167-174, vol. 279, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Wang, et al., A General Cone-Beam Reconstruction Algorithm, IEEE Transactions on Medical Imaging, Sep. 1993, pp. 486-496, vol. 12, No. 3.
Wang, Ge, X-Ray micro-CT with a displaced detector array, Medical Physics, Jul. 2002, pp. 1634-1636, vol. 29, No. 7.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Invitation to Pay Additional Fees from PCT/US2022/035500 dated Oct. 13, 2022, 14 pages.
European Search Report from EP 23155102.9 dated Jul. 4, 2023.
Office Action from Japanese Application No. 2021-531086 dated Jul. 11, 2023, 3 pages.
Office Action from European Application No. 19824059.0 dated Jul. 18, 2023, 4 pages.
Office Action from European Application No. 19824061.6 dated Jul. 24, 2023, 4 pages.
Office Action from Japanese Application No. 2021-531085 dated Jul. 25, 2023, 8 pages.
Office Action from Japanese Application No. 2021-531084 dated Jul. 25, 2023, 8 pages.
Office Action from Japanese Application No. 2021-521836 dated Aug. 15, 2023, 19 pages.
Notice of Allowance from U.S. Appl. No. 17/479,645 dated Sep. 27, 2023, 78 pages.
Office Action from Japanese Application No. 2021-521751 dated Aug. 29, 2023, 5 pages.
Office Action from Japanese Application No. 2021-521845 dated Aug. 29, 2023, 4 pages.
Office Action from Japanese Application No. 2021-521752 dated Sep. 19, 2023, 4 pages.

(56) References Cited

OTHER PUBLICATIONS

Office Action from Japanese Application No. 2021-521849 dated Sep. 26, 2023, 4 pages.
Office Action from Japanese Application No. 2021-531088 dated Sep. 26, 2023, 14 pages.
Office Action from Japanese Application No. 2021-521757 dated Oct. 3, 2023, 18 pages.

* cited by examiner

SPARSE BACKGROUND MEASUREMENT AND CORRECTION FOR IMPROVING IMAGING

CROSS-REFERENCE TO RELATED APPLICATIONS

This application is related to U.S. patent application Ser. No. 16/694,148, to D. Gagnon et al., "APPARATUS AND METHODS FOR SCALABLE FIELD OF VIEW IMAGING USING A MULTI-SOURCE SYSTEM," filed on Nov. 25, 2019. This application also relates to eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including Ser. No. 16/694,145, filed Nov. 25, 2019, entitled "MULTIMODAL RADIATION APPARATUS AND METHODS;" Ser. No. 16/694,161, filed Nov. 25, 2019, entitled "INTEGRATED HELICAL FAN-BEAM COMPUTED TOMOGRAPHY IN IMAGE-GUIDED RADIATION TREATMENT DEVICE;" Ser. No. 16/694,166, filed Nov. 25, 2019, entitled "COMPUTED TOMOGRAPHY SYSTEM AND METHOD FOR IMAGE IMPROVEMENT USING PRIOR IMAGE;" Ser. No. 16/694,177, filed Nov. 25, 2019, entitled "OPTIMIZED SCANNING METHODS AND TOMOGRAPHY SYSTEM USING REGION OF INTEREST DATA;" Ser. No. 16/694,190, filed Nov. 25, 2019, entitled "HELICAL CONE-BEAM COMPUTED TOMOGRAPHY IMAGING WITH AN OFF-CENTERED DETECTOR;" Ser. No. 16/694,192, filed Nov. 25, 2019, entitled "MULTI-PASS COMPUTED TOMOGRAPHY SCANS FOR IMPROVED WORKFLOW AND PERFORMANCE;" Ser. No. 16/694,202, filed Nov. 25, 2019, entitled "METHOD AND APPARATUS FOR SCATTER ESTIMATION IN CONE-BEAM COMPUTED TOMOGRAPHY;" Ser. No. 16/694,210, filed Nov. 25, 2019, entitled "ASYMMETRIC SCATTER FITTING FOR OPTIMAL PANEL READOUT IN CONE-BEAM COMPUTED TOMOGRAPHY;" Ser. No. 16/694,218, filed Nov. 25, 2019, entitled "METHOD AND APPARATUS FOR IMPROVING SCATTER ESTIMATION AND CORRECTION IN IMAGING;" and Ser. No. 16/694,230, filed Nov. 25, 2019, entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to patient imaging using x-ray radiation during, before, and after radio therapy (RT). The disclosed technology relates, in particular, to removing residual effects caused by charging certain x-ray detectors. It further relates to measuring background radiation and using the background radiation to correct detected images.

BACKGROUND

External beam radiation therapy provides a non-invasive alternative to riskier, more invasive surgery. It can treat pathological anatomies (e.g., tumors, lesions, vascular malformations, nerve disorders, etc.) with x-rays generated by a therapeutic radiation source, such as a linear accelerator (LINAC). Typically, a source directs x-ray beams at a tumor site from multiple angles. Careful control of the source's orientation can insure that each x-ray beam passes through the same tumor site, but through a different area of neighboring healthy tissue. This keeps the cumulative radiation dose at the tumor high while keeping the dose in healthy tissue relatively low.

"Radiosurgery" refers to applying radiation to a target region at doses sufficient to necrotize a pathology more quickly than radiotherapy. It applies higher radiation doses per fraction (e.g., 500-2000 centigray) and hypo-fractionation (e.g., one to five fractions or treatment days). In contrast, radiotherapy may use 100-200 centigray and hyper-fractionation (e.g., 30 to 45 fractions). X-ray sources for radiotherapy and radiosurgery tend to be in MeV range. This is higher energy than x-ray sources for imaging, which tend to be in the keV range. The terms "radiation treatment" and "radiation therapy" are used interchangeably herein to mean radiosurgery and/or radiotherapy unless otherwise noted, for convenience in contrasting these two MeV techniques with imaging techniques using keV x-rays. Note that, herein, "MV" and "MeV" x-rays and sources are referred to interchangeably, as are "kV" and "keV" x-rays and sources per convention. When x-ray and source energies are specifically referred to, "MeV" and "keV" are used.

Image-guided radiation therapy (IGRT) systems combine keV and MeV sources for imaging and treatment. IGRT systems are typically classified by how they mount and move the therapeutic x-ray sources. In gantry IGRTs, a gantry rotates the therapeutic radiation source around an axis passing through an "isocenter," or point of intersection of x-ray beams. The results in x-ray beam intersection in a 3D volume in the shape of a sphere or ellipsoid. Different types of gantries mount and move x-ray sources differently. C-arm gantries mount the therapeutic radiation source in a cantilever and rotate it about an axis passing through the isocenter. Ring gantries mount the therapeutic source to a toroidal or ring shaped element. The patient's body extends through the hole in the toroid or ring. The toroid or ring rotates about an axis passing through the isocenter. In robotic arm-based systems, mounting the therapeutic radiation source on a robotic arm gives its motion more degrees of freedom. The robotic arm extends over and around the patient. It can provide at least five degrees of freedom to deliver therapeutic radiation from multiple out-of-plane directions. In contrast, ring or C-arm systems deliver therapeutic radiation with a set angle defined by the rotational trajectory of the radiation source.

X-ray imaging systems can be incorporated into radiation therapy systems to guide radiation delivery. They can also track in-treatment target motion. MeV imaging systems can place a detector opposite the therapeutic source to image the patient for setup and in-treatment images. Other approaches use distinct, independent image radiation source(s) and/or detector(s) for patient set-up and in-treatment images. Comparing in-treatment images to prior or pre-treatment image information allows tracking of the target during treatment. Pre-treatment image information may comprise, for example, CT data, cone-beam CT (CBCT) data, magnetic resonance imaging (MRI) data, positron emission tomography (PET) data or 3D rotational angiography (3DRA) data, and any information obtained from these imaging modalities (for example and without limitation, digitally reconstructed radiographs (DRRs)).

As discussed above, typically, keV x-ray sources are used for imaging. keV sources tend to provide good contrast with most kinds of soft tissue. However, keV systems do not perform as well when the imaging zone includes more dense tissue (e.g., thick bones, calcified arteries, etc.). When tissue of interest lies within the same irradiated area as these dense materials, keV images can suffer defects caused by the interactions of the keV x-rays and the dense material. Streak artifacts may obscure or darken areas of interest. Metal (e.g., in dental fillings, implants, or stents) along an x-ray path can cause photon starvation, obscuring regions of interest. Scattering errors and other issues may cause additional problems. Another significant problem is "beam hardening," where certain portions of the body "see" a different x-ray photon spectrum due to selective absorption in other portions of the body.

MeV x-ray sources primarily used for treatment can also generate images. However, the contrast-to-noise ratio (CNR) in MeV images can be low. There are indeed some tissues whose native contrast is better in the keV range and others where it is better in the MeV. But at matched dose, which is a key factor in patient imaging, there will be fewer MeV x-rays. Also, MeV x-rays are more difficult to detect, leading to higher noise in those measurements. This makes MeV CNR generally worse for all tissues.

Crude MeV x-rays images are often used to determine the location of the MeV treatment beam with respect to the patient. Yet there is untapped potential for more ambitious MeV imaging applications. In particular, combining keV and MeV x-ray imaging in a single therapeutic device can use the complimentary advantages of both energy ranges. For example, contrast from MeV x-rays could fill in gaps in keV images where denser tissue degrades keV imaging contrast. Therefore, refined and improved techniques for combining information from both types of images are disclosed below.

Each of the systems discussed above can present problems in image gathering and analysis. For example, x-rays used in keV imaging can create transient effects on detectors that can last for more than one image scan. This creates anomalous features in the images from the subsequent scans that can occlude features of the image and confound analysis. These effects can be observed in high energy MeV x-rays used in radiotherapy for certain detectors are used that are prone to charging and other residual effects.

BRIEF SUMMARY

According to aspects of the present disclosure, an imaging system includes a first x-ray source configured to produce first x-ray photons in a first energy range suitable for imaging, project the first x-ray photons onto an area designated for imaging, a rotatable gantry configured to rotate the first x-ray source such that the first x-ray source traverses an angular path, and a data processor having an analytical portion. The analytical portion is configured to collect first data relating to the transmission of the first x-ray photons through the area designated for imaging at a set of image-collection angles along the angular path, collect background data at a set of background-collection angles along the angular path, wherein the number of image-collection angles is maximized between background-collection angles. The analytical portion is also configured to remove errors in the first data using the background data, and generate a corrected image based on the removal of errors in the first data.

The analytical portion may determine the set of background-collection angles at least in part by determining a minimum number of background measurements. The analytical portion may determine the set of background-collection angles at least in part by maximizing the set of image collection angles between the background-collection angles. Removing errors from the first data using the background data may include weighting images using a measured time-decay response of an x-ray detector and subtracting the weighted images from the first data. The analytical portion may recalibrate the time-decay response based on the background data. Recalibrating the time-decay response may be based on more than one background image and includes more than one decay term. Removing errors in the first data using the background data may include interpolating background images.

Variations include an imaging system including an x-ray source configured to produce x-ray photons in an energy range suitable for imaging, project the x-ray photons onto an area designated for imaging, a rotatable gantry configured to rotate the x-ray source such that the first x-ray source traverses an angular path. The system includes a data processor having an analytical portion configured to collect background data at a first angle along the angular path, collect image data relating to the transmission of the x-ray photons through the area designated for imaging over a range of angles along the angular path, collect background data at a second angle along the angular path, the second angle positioned such that the range of angles may be between the first and second angles, generate a corrected image by removing errors in the image data using an interpolation of the background data collected at the first and second angles.

The analytical portion may determine the first angle, the second angle, and the range of angles at least in part by determining a minimum number of background measurements for accurate background estimation. The analytical portion may determine the first angle, the second angle, and the range of angles at least in part by maximizing at least one of a total number of images of the designated area for imaging and a number of images of the designated area for imaging taken between each of the background-collection angles. Removing errors from the image data may include weighting images using a measured time-day response of an x-ray detector and subtracting the weighted images from the first data. The analytical portion may recalibrate the time-decay response based on the background data. The system may include a Cone-Beam Computed Tomography (CBCT) system. The system may include a second x-ray source configured to produce second x-ray photons in a second energy range different in energy than the first energy range, project the second x-ray photons onto an area designated for imaging, and wherein the analytical portion may be configured to at least one of combine data derived from the first and second x-ray photons, interleave application of the first and second x-ray sources, and concurrently operate the first and second x-ray sources. The set of background-collection angles may be evenly distributed along the angular path. The set of background-collection angles may be distributed at pre-determined angles along the angular path. The set of background-collection angles may be determined via at least one of analyzing a planning computed tomography (CT) image, analyzing a previously available CT image, analyzing a CT 2D survey image, analyzing an image in orthogonal angles, analyzing a patient atlas, analyzing data during acquisition.

The set of background-collection angles may be determined using at least one of a patient geometry, an acquisition protocol, and a projection angle relative to patient orientation. The analytical portion may determine the set of background-collection angles via an algorithm. The algorithm may determine the set of background collection angles based on improving accuracy of CBCT reconstruction. The algorithm may exclude conjugate angles from the set of background collection angles. The algorithm may select background collection angles based at least in part on the use of MeV radiation. The algorithm may select background collection angles to improve at least one of lag correction and data-driven scatter correction. Removing errors in the first data using the background data may include collecting background data at a first angle along the angular path, collecting the first data at a range of angles along the angular path, collecting background data at a second angle along the angular path, the second angle positioned such that the range of angles may be between the first and second angles, generating an error image by interpolating the background data collected at the first and third angles, and removing errors in the first data using the error image.

The algorithm may generate a first set of background collection angles for a first scan and a second set of background collection angles for a second scan, and the first and second sets may be different. The first and second sets may not overlap. The angular path may be helical. The algorithm may determine the background collection angles at least in part based on a pitch size of the helix. The algorithm may determine the background collection angles at least in part based on improving the accuracy of a 3D image reconstruction using the image data. An image reconstruction may select a different set of background collection angles for different rotations of the first source. The analytical portion may synchronize an x-ray control, a flat panel detector readout, and a CT scan control so that the flat panel detector readout will provide background data when the first x-ray source may be powered off. A movement of the first x-ray source along the angular path may be uninterrupted while the x-ray source may be powered off. The analytical portion may be further configured to generate a 3D reconstruction by modifying a reconstruction algorithm based on the background collection angles.

Modification accounts for an uneven spacing between background collection angles and an uneven spacing between image collection angles. Modification considers a difference between azimuth angular positions of background images in a first rotation of the first x-ray source and azimuth angular positions of background images in a second rotation of the first x-ray source. The azimuth angular positions of the first rotation may be interleaved with the azimuth angular positions of the second rotation. A method of an operating an imaging system including producing first x-ray photons in a first energy range suitable for imaging, projecting the first x-ray photons onto an area designated for imaging, rotating the first x-ray source such that the first x-ray source traverses an angular path, collecting first data relating to the transmission of the first x-ray photons through the area designated for imaging at a set of image-collection angles along the angular path, collecting background data at a set of background-collection angles along the angular path, wherein the system acquires more than one image of the designated area for imaging between background angles, removing errors in the first data using the background data, and generating a corrected image based on the removal of errors in the first data.

Variations include an imaging system including a first x-ray source configured to produce first x-ray photons in a first energy range suitable for imaging, project the first x-ray photons onto an area designated for imaging, a rotatable gantry configured to rotate the first x-ray source such that the first x-ray source traverses an angular path, and a data processor having an analytical portion configured to collect first data relating to the transmission of the first x-ray photons through the area designated for imaging at a set of image-collection angles along the angular path, collect background data at a background-collection angle along the angular path, remove errors in the first data using the background data, and generate a corrected image based on the removal of errors in the first data.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
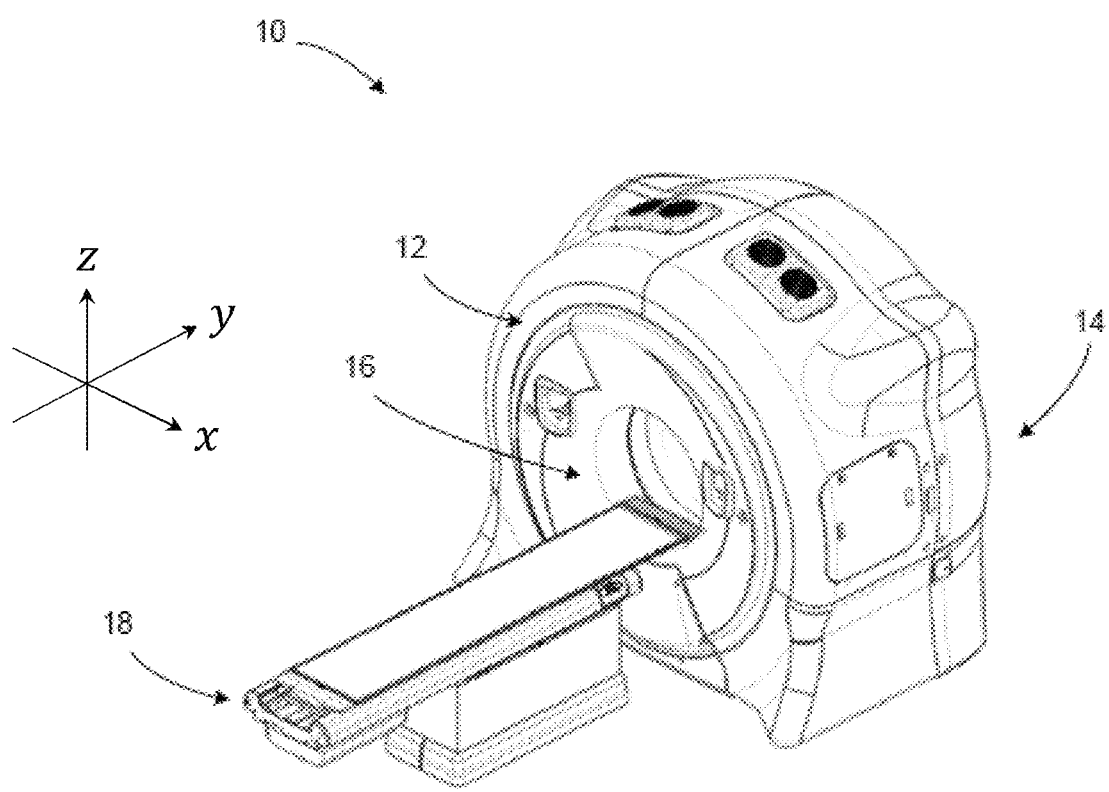
FIG. 1 is a perspective view of an exemplary multimodal radiotherapy apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to multimodal imaging/radiotherapy devices and methods. In some embodiments, a radiotherapy delivery device and method can make use of an integrated low-energy radiation source for imaging and a high-energy radiation source for treatment and/or imaging in conjunction with or as part of IGRT. In particular, for example, a radiotherapy delivery device and method can combine a low-energy collimated radiation source for imaging in a gantry using rotational (e.g., helical or step-and-shoot, with or without the ability to rotate continuously with the use of a slip-ring) image acquisition along with a high-energy radiation source for imaging and/or therapeutic treatment.

Complementary information and advantages can be exploited from a keV radiation source and an MeV radiation source. For example, the intrinsic contrast of soft tissues may be higher at low-energies, while there is no starvation of primary photons through wide or dense structures at high-energies. keV and MeV imaging data can be used to supplement each other to yield higher quality images. High quality volume imaging can be needed for visualization of targets and organs-at-risk (OARS), for adaptive therapy monitoring, and for treatment planning/re-planning. In some embodiments, the multimodal system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the multimodal apparatus collimates a radiation source, including, for example, into a cone beam or a fan beam using, for example, a beamformer (which may include a collimator) to limit the beam. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high frame rates, and/or sparse data reconstruction techniques, to provide CT quality imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas.

The multimodal apparatus and methods can provide selective and variable collimation of a radiation beam emitted by the source of radiation, including adjusting the radiation beam shape to expose less than the entire active area of an associated radiation detector (e.g., a radiation detector positioned to receive radiation from the x-ray radiation source). Also, exposing only a primary region of the detector to direct radiation allows shadowed regions of the detector to receive only scatter. In some embodiments, scatter measurements in the shadow region (and in some embodiments measurements in the penumbra region) of the detector can be used to estimate scatter in the primary region of the detector receiving projection data.

The multimodal apparatus and method can provide selective and variable detector readout areas and ranges, including adjusting the detector readout range to limit the active area of the detector for improved readout speed. For example, less than the available shadow region data may be read and used for scatter estimation. Combining selective readout with beamforming allows for various optimizations of scatter fitting techniques.

Some exemplary aspects of the apparatus that may implement the disclosed embodiments follow. It should be understood that the embodiments are not limited to the specific hardware and apparatuses disclosed herein. For example, any of the methods and algorithms disclosed herein may be implemented by the apparatuses disclosed in U.S. patent application Ser. No. 16/694,148, filed on Nov. 25, 2019, herein incorporated by reference in its entirety.

Figure 2A:
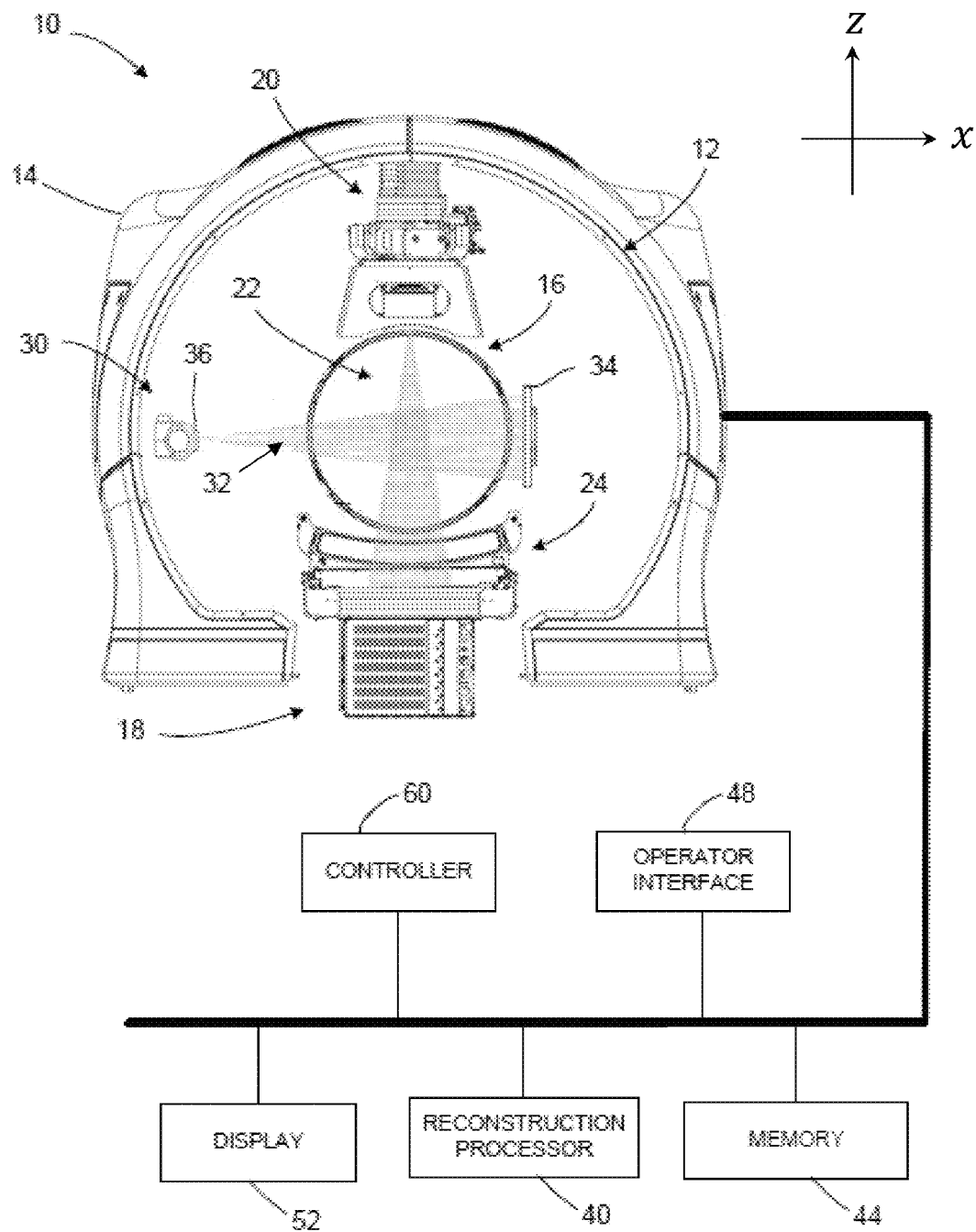
FIG. 2A is a diagrammatic illustration of an exemplary multimodal radiotherapy apparatus in accordance with one aspect of the disclosed technology.

With reference to FIG. 1 and FIG. 2A, a multimodal apparatus 10 is shown. It will be appreciated that the multimodal apparatus 10 may be associated with and/or integrated into a radiotherapy device (as shown in FIG. 2A)

that can be used for a variety of applications, including, but not limited to IGRT, for example, as an IGRT delivery system (e.g., IGRT delivery system 104 shown in FIG. 3A and discussed in detail below). The multimodal apparatus 10 includes a rotatable gantry system, referred to as gantry 12, supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, keV and MeV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of radiation sources and associated radiation detector(s) while providing sufficient bandwidth for the high-quality imaging data received by the detector(s). A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system. As mentioned above, a major issue with single rotation CBCT is insufficient sampling on all slices except for the central slice (the one containing the rotation). This can be overcome by helical trajectory cone-beam imaging.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

As shown in FIG. 2A, the multimodal apparatus 10 includes a low-energy radiation source (e.g., keV) 30 coupled to or otherwise supported by the rotatable gantry 12. In this embodiment, the low-energy radiation source 30 is a source of imaging radiation and emits a radiation beam (indicated generally as 32) for generating high-quality images. In this embodiment, the source of imaging radiation is an x-ray source 30, configured as a kilovoltage (keV) source (e.g., a clinical x-ray source having a voltage in the range of about 20 keV to about 150 keV). In one embodiment, the keV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @ about 70 keV and @ about 82 keV), etc.). References herein to x-ray, x-ray imaging, x-ray imaging source, etc. are exemplary for particular embodiments. Other imaging transmission sources can be used interchangeably in various other embodiments. An x-ray detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30.

It will be appreciated that the x-ray detector 34 can take on a number of configurations without departing from the scope of the disclosed technology. As illustrated in FIG. 2A, the x-ray detector 34 can be configured as a flat-panel detector (e.g., a multi-row flat panel detector). In accordance with another exemplary embodiment, the x-ray detector 34 can be configured as a curved detector. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the low-energy radiation source 30 rotates around and emits radiation toward the patient.

Although FIGS. 1 and 2 depict a multimodal apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and/or translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which may be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task and scatter estimation process being carried out, including, for example, combinations of narrow and wide FOV scans. The apparatus 10 has the ability to acquire both single rotation cone beam and wide and narrow beam angle cone beam images, helical or other.

The beamformer 36 may be configured in a variety of ways that allow it to adjust the shape of the radiation beam 32 emitted by the x-ray source 30. For example, the beamformer 36 can be configured to include a set of jaws or other suitable members that define and selectively adjust the size of an aperture through which the radiation beam from the x-ray source 30 may pass in a collimated manner. In accordance with one exemplary configuration, the beamformer 36 can include an upper jaw and a lower jaw, where the upper and lower jaws are movable in different directions (e.g., parallel directions) to adjust the size of the aperture through which the radiation beam from the x-ray source 30 passes, and also to adjust the beam 32 position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 2A, the multimodal apparatus 10 may be integrated with a radiotherapy device that includes a high-energy radiation source (e.g., MeV) 20 coupled to or otherwise supported by the rotatable gantry 12. In accordance with one embodiment, the high-energy radiation source 20 is configured as a source of therapeutic radiation, such as a high-energy source of radiation used for treatment of a tumor within a patient in a region of interest. In other embodiments, the high-energy radiation source 20 is also configured as a source of imaging radiation, or at least utilized as such. It will be appreciated that the source of therapeutic radiation can be a high-energy x-ray beam (e.g., MeV x-ray beam), and/or a high-energy particle beam (e.g., a beam of electrons, a beam of protons, or a beam of heavier ions, such as carbon) or another suitable form of high-energy radiation. In one embodiment, the high-energy radiation source 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the high-energy radiation source 20 has a higher energy level (peak and/or average, etc.) than the low-energy radiation source 30.

In one embodiment, the high-energy radiation source 20 is a LINAC producing therapeutic radiation (e.g., MeV) and the imaging system comprises an independent low-energy radiation source 30 producing relatively low intensity and lower energy imaging radiation (e.g., keV). In other embodiments, the therapeutic radiation source 20 could be a radioisotope, such as, for example, Co-60, which can generally have energy >1 MeV. The high-energy radiation source 20 can emit one or more beams of radiation (indicated generally by 22) toward a region-of-interest (ROI) within a patient supported on the patient support 18 in accordance with a treatment plan.

In various embodiments, the high-energy radiation source 20 is utilized as a source of therapeutic radiation and a source of imaging radiation. As discussed in detail below, sources of radiation 20, 30 may be used in conjunction with one another to provide higher quality and better utilized images. References to the therapeutic radiation source 20 herein are to distinguish the high-energy radiation source 20 from the low-energy radiation source 30, which may be used only for imaging. However, references to the therapeutic radiation source 20 include embodiments where the therapeutic radiation source 20 (high-energy radiation source) can be utilized for therapy and/or imaging. In other embodiments, at least one additional radiation source can be coupled to the rotatable gantry 12 and operated to acquire projection data at a peak photon energy distinct from the peak photon energies of sources of radiation 20, 30.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The beamformer associated with the therapeutic radiation source 20 can be configured in a number of ways, similar to the beamformer 36 associated with the imaging source 30. For example, a beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be incrementally reduced by offsetting the radiation planes. In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MeV scatter on a keV detector.

When integrated with a radiotherapy device, multimodal apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, cone-beam CT data, MRI data, PET data or 3D rotational angiography (3DRA) data, and/or any information obtained from these or other imaging modalities. In some embodiments, the multimodal apparatus 10 can track in-treatment patient, target, or ROI motion.

A reconstruction processor 40 can be operatively coupled to detector 24 and/or detector 34. In one embodiment, the reconstruction processor 40 is configured to generate patient images based on radiation received by the detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The multimodal apparatus 10 can include an operator/user interface 48, where an operator of the apparatus 10 can interact with or otherwise control the apparatus 10 to provide input relating to scan or imaging parameters and the like. The operator interface 48 can include any suitable input devices, such as a keyboard, mouse, voice-activated controller, or the like. The apparatus 10 can also include a display 52 or other human-readable element to provide output to the operator of the apparatus 10. For example, the display 52 can allow the operator to observe reconstructed patient images and other information, such as imaging or scan parameters, related to operation of the apparatus 10.

As shown in FIG. 2A, the multimodal apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer controller, a controller coupled to the detector 24 and/or the x-ray detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, a multimodal apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with the apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with apparatus 10.

Multimodal apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented. For example, in various embodiments, the radiation sources 20, 30 can be operated such that the measured projection data from the radiation sources 20, 30 are acquired simultaneously (or essentially/nearly (quasi-) simultaneous, e.g., within about 50 ms of each other) or sequentially (e.g., separated by seconds, minutes, etc.)

It will be appreciated that radiation sources 20, 30 and detector(s) 24, 34 can be configured to provide rotation around the patient during an imaging and/or treatment scan in a number of ways. In one embodiment, synchronizing the motion and exposure of the source 20, 30 with the longitudinal motion of the patient support 18 can provide a continuous helical acquisition or scan of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The multimodal apparatus 10 is capable of volume-based and planar-based imaging acquisitions. For example, in various embodiments, the multimodal apparatus 10 may be used to acquire volume images and/or planar images and execute the associated processing, including scatter estimation/correction methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of apparatus 10 described above.

In one embodiment, the gantry 12 rotation speed, the patient support 18 speed, the beamformer shape, and/or the detector readout could all be constant during image acquisition. In other embodiments, one or more of these variables could change dynamically during image acquisition and/or treatment. The gantry 12 rotation speed, patient support 18 speed, beamformer shape, and/or detector readout can be varied to balance different factors, including, for example, image quality, image acquisition time, dosage, workflow, etc.

In other embodiments, these features can be combined with one or more other image-based activities or procedures, including, for example, patient set up, adaptive therapy monitoring, treatment planning, etc.

Residual Images, Lag, and Ghosting

Apparatuses such as apparatus 10 and other CT scan devices typically use detectors like detector 34 comprising flat panels. This is the configuration shown in FIG. 2B.

Figure 2B:
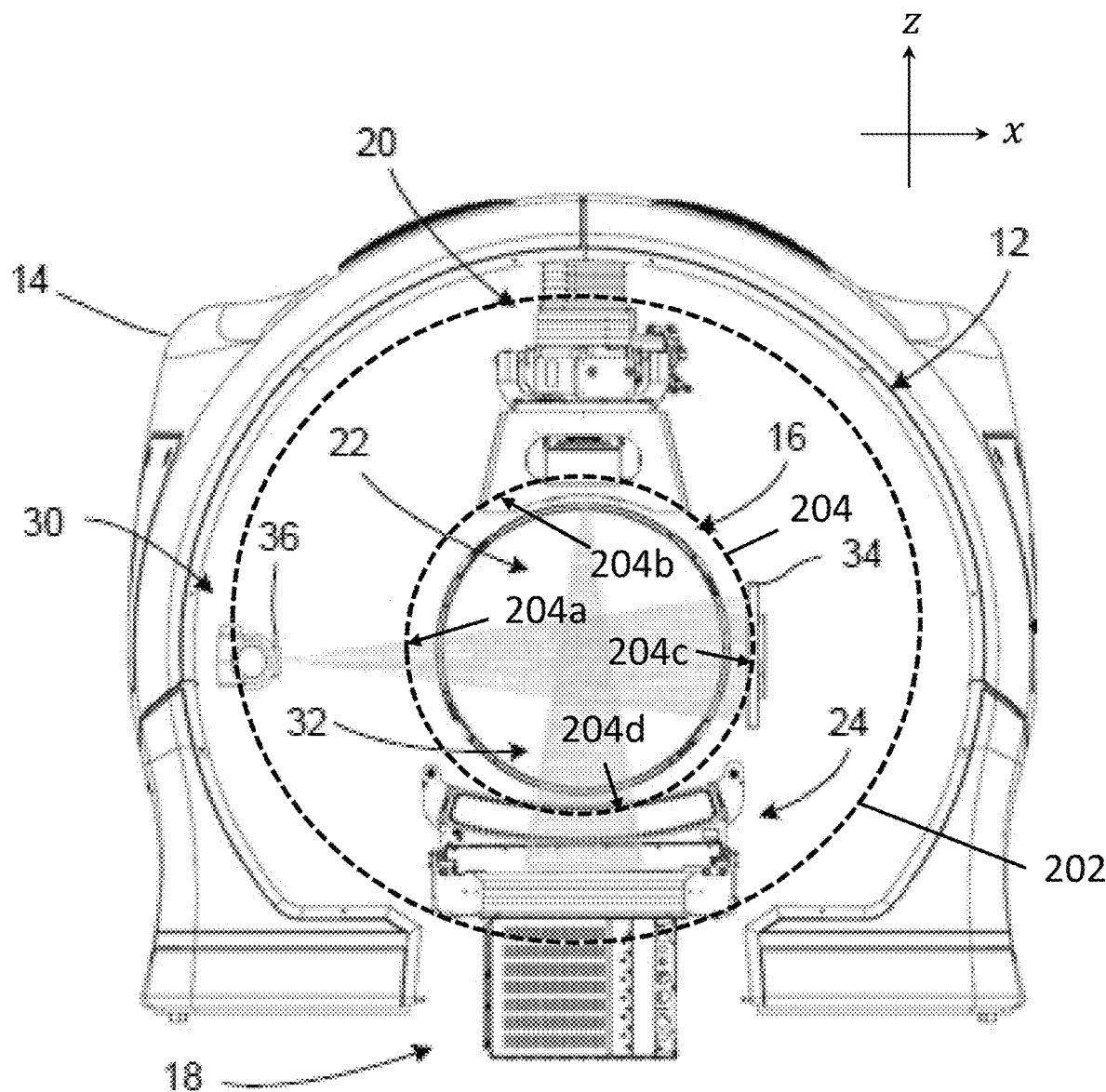
FIG. 2B shows a rotating path 202 for source 30 and rotating path 204 for detector 34 in gantry 12.

During image data acquisition, both the source (e.g., source 30) and detector (e.g., 34) move along an angular path as the gantry 12 rotates. FIG. 2B shows the angular path 202 for the source 36 and corresponding angular path 204 for detector 34. Source 36 and detector 34 may move along their respective paths in a synchronized manner. Data is collected at various positions along the angular path, e.g., positions 204a-204d.

At each position 204a-204d, the detector will spend a period of time to collect an appropriate type of data. The data type may be image data I, which is data relating to the traversal of x-ray from source 36 through an object of interest (not shown). Image data I tends to be diagnostic data related to a patient. However, other data may be obtained in the context of the present disclosure. Image data I can be reconstructed to form a 3D representation of the patient using tomographic methods. To detect image I data, source 36 must be powered up and emitting x-rays. Alternatively, the data type may be background B data. Background B data is what detector 34 detects when the source 36 is powered off. The source of background B data may be residual effects of x-ray on the detector, as discussed in more detail below.

For a number of reasons, flat panels detectors (e.g., detector 36) tend to be made using materials that can trap charge created by the x-ray interaction with the detector. One example of such materials is amorphous silicon. This charge trapping can lead to residual or "ghosting" afterglow effects from one image I data collection to the next as detector 34 traverses angular path 204. Ghosting is spurious signal during image I data acquisition that corresponds to lingering radiation effects from prior image I data acquisitions. It may significantly degrade image quality and frustrate quantification. Although charge trapping is described here in the context of flat panel detectors and those made of amorphous silicon, it is to be understood that charge trapping is general and can happen in other systems, such as silicon photon multipliers (SiPMs). It is to be understood that methods and solutions for ghosting applied herein are not specific to detector type or material. They can be applied using any detector that exhibits charge trapping effects.

Residual signal due to charge trapping can be detected in the current frame from detector exposure in the previous frame. When a large angular range is scanned over a short time (e.g., angular path 204 is scanned over minutes or seconds), ghosting from x-ray exposure in the angles at the beginning of the range (e.g., position 204a) can degrade the signal in the angles at the later end of the range (e.g., position 204d). This can introduce artifacts in reconstructed images. Examples of such artifacts include contrast reduction, image non-uniformity, CT number bias (error), and skin-line artifacts.

Ghosting can be particularly acute in IGRT systems (e.g., apparatus 10) including MV x-ray sources (e.g., source 20) since these produce such high energy beams. MeV CT (MVCT) systems can cause cross contamination in which scatter from an MV beam contaminates a Cone-Beam Computed Tomography (CBCT) image. This tends to degrade the quality and quantitation of CBCT images. Such effects impact CBCT imaging in different ways, including by deteriorating the acquired data and adversely impact scatter correction using collimator shadow fitting. In radiotherapy (RT) systems with an MeV beam, if the keV imaging detector is not adequately shielded from the MeV scatter and the keV imaging time is close to the MeV beam on/off cycle, scatter from MeV may cause significant lag and ghosting in keV images. If the MeV beam is turned on while keV imaging is acquiring data, the scatter from the MeV beam may directly deteriorate the keV signal acquired while the MeV beam is on. The lag and ghosting may impact more keV data after the MeV beam is turned off.

When using a collimator shadow fitting approach for scatter correction, lag and ghosting can degrade the data in the collimator shadows. This can lead to incorrect fitting and incorrect estimation of the scatter in the collimator opening area. The incorrect fitting/estimation can result in the scatter correction for CBCT imaging becoming inaccurate.

In a conventional lag correction, images from angles preceding the current imaging angle are weighted by a measured time-decay response of the detector. The weighted images are then subtracted from the current image. Challenges in this approach include that the conditions during measurement of the pre-determined time-decay response may not match the situation for patient studies with highly non-uniform structures and contrasts. These conditions include energy of the x-ray, the intensity of the x-ray illuminating on the detector. Another challenge is that the time interval used for lag correction is empirically determined based on the time-decay response. A large time interval can degrade accuracy of lag estimation and correction. Still another challenge occurs when an MeV beam is turned on (e.g., in an RT scenario) while the CBCT detector is acquiring data. This causes down scatter from the MeV beam to flush the CBCT detector, resulting in a severe lag effect for the data in the subsequent acquisition angles. The conventional lag correction approach may become inaccurate.

Figure 2C:
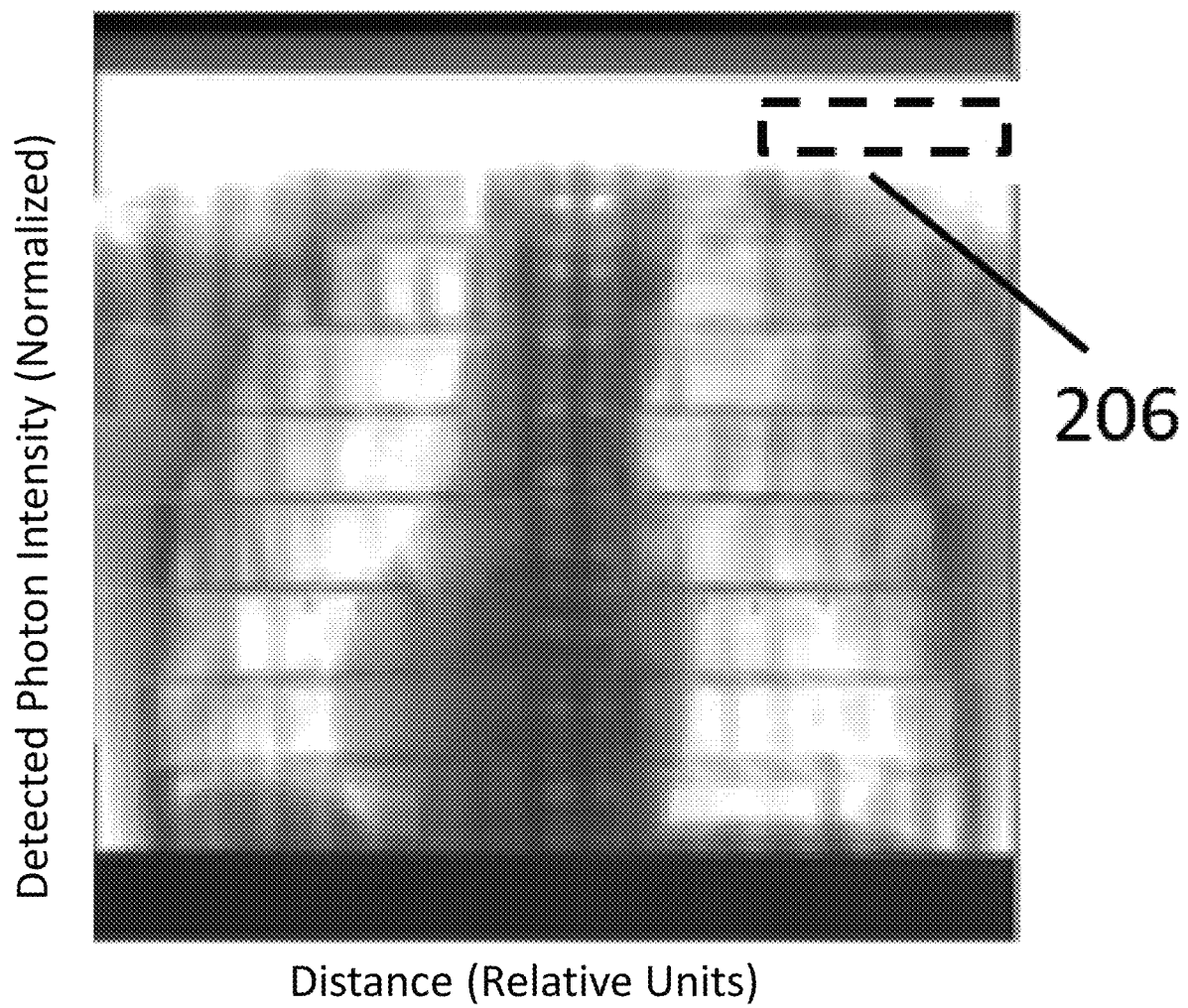
FIG. 2C shows an image taken with an energy intensive region 206 causing a charging or ghosting effect on subsequent images.
Figure 2D:
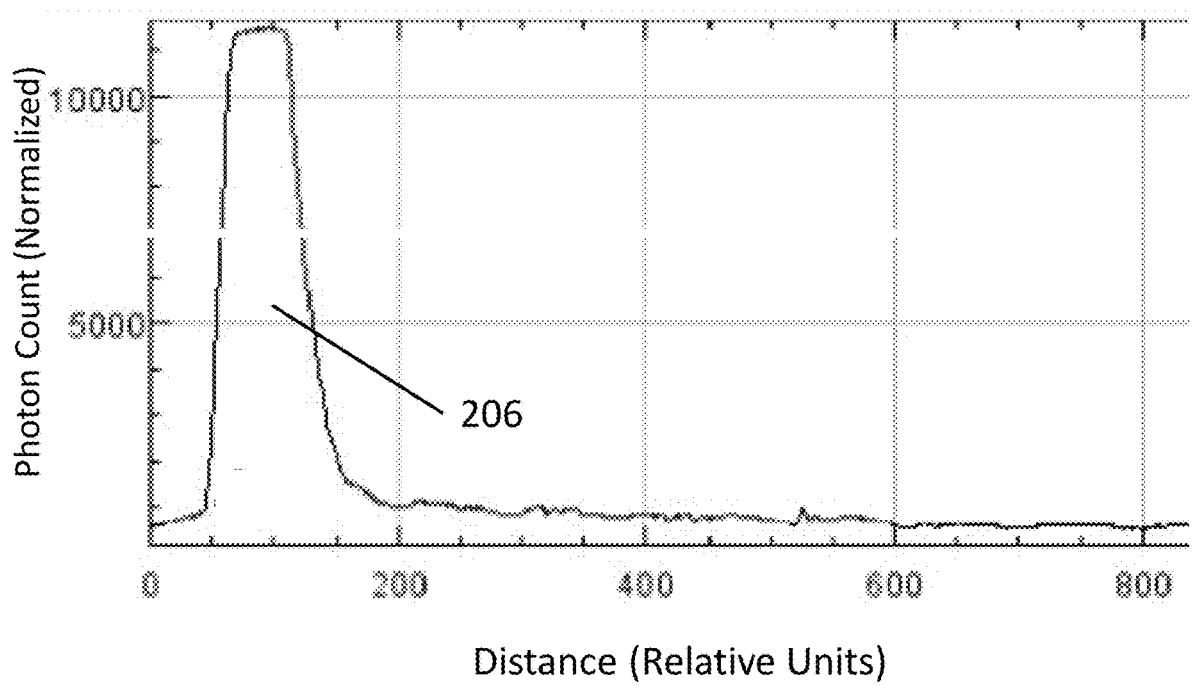
FIG. 2D is an intensity profile of the image in FIG. 2C showing the energy intensive region 206
Figure 2E:
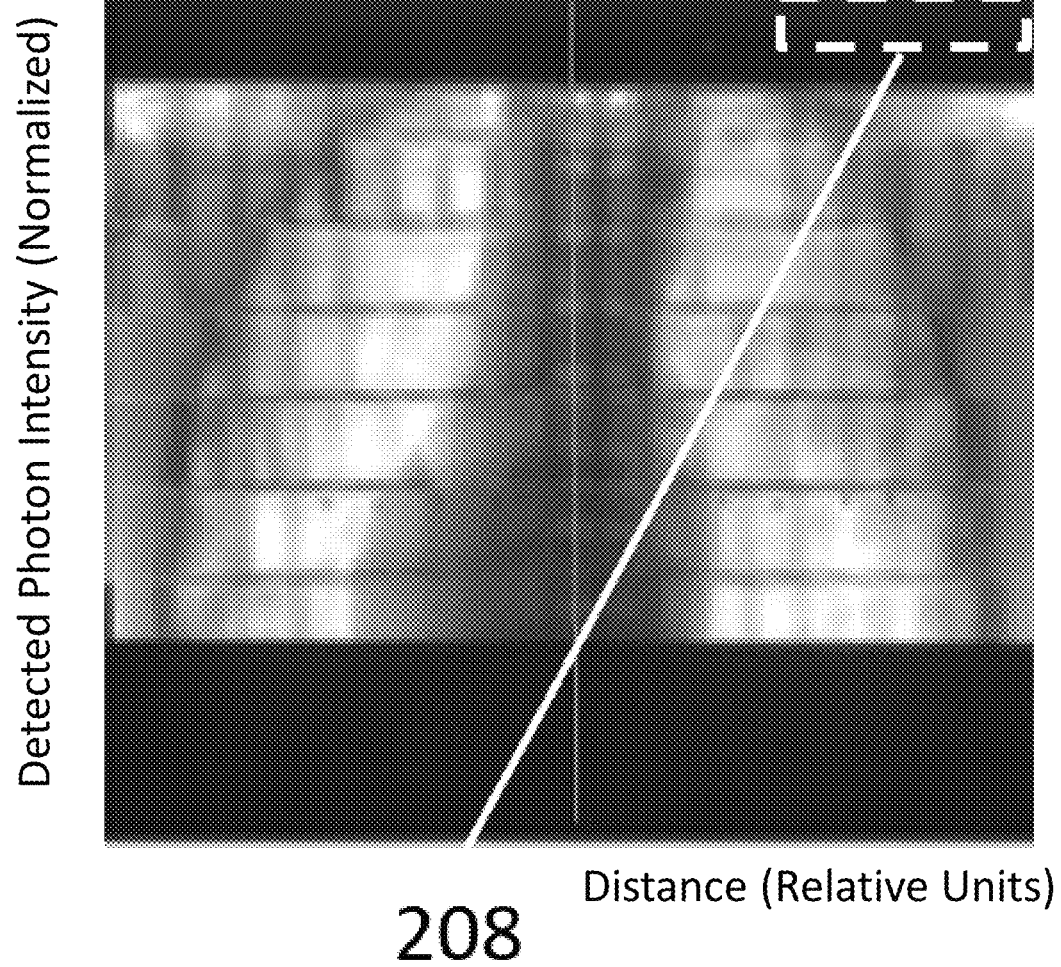
FIG. 2E is an image taken subsequent to the image in FIG. 2C having a residual or ghosting effect 208 caused by the high energy region 206 in FIG. 2C.
Figure 2F:
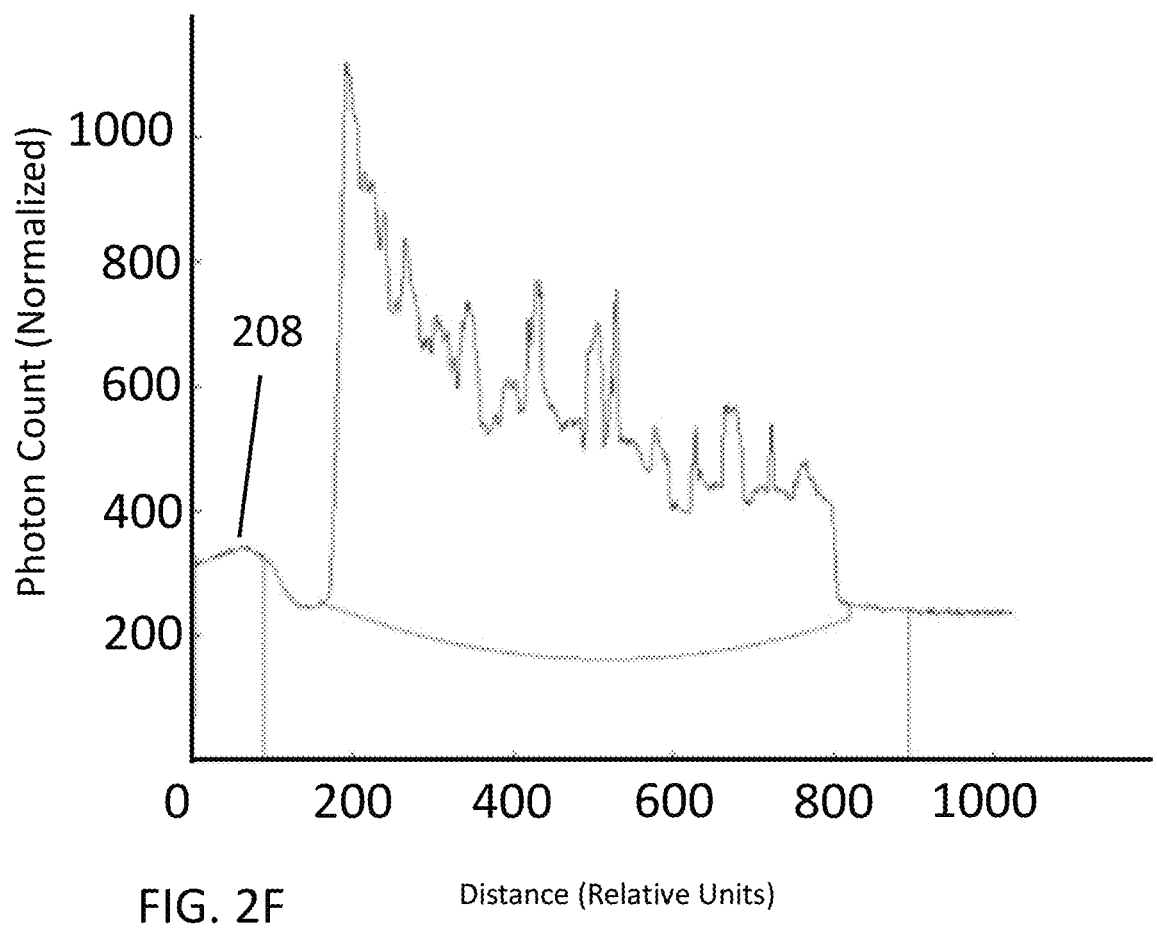
FIG. 2F is a profile of the image in FIG. 2E showing the residual or ghosting effect 208.

FIGS. 2C-2F show an exemplary lag-introduced problem with a data-driven scatter correction approach for CBCT in the context of the present disclosure. FIG. 2E shows an object image acquired 1.5 minutes after the image in FIG. 2C. FIG. 2D shows the profile of the image in FIG. 2C. FIG. 2E shows the profile of the image in FIG. 2D. Note that the coordinate direction on the distance axis is transposed between FIGS. 2C and 2D. It is also reversed between FIGS. 2E and 2F. This is why features 206 and 208 appear on the top of FIGS. 2C and 2E, respectively, but appear on the left sides of FIGS. 2D and 2F.

More specifically, the image in FIG. 2C was taken with a collimator (not shown) having a relatively wide opening. This wide opening caused the area 206 to be directly illuminated by the x-ray source (e.g., source 30). The illumination was so intense that charging occurred on the detector (e.g., detector 34). The charging creates an image lag between FIGS. 2C and 2E. The lag manifests as increase 208 in detected photon intensity in FIG. 2E (profile FIG. 2F), despite FIG. 2E being acquired more than a minute after FIG. 2C. Increase 208 directly corresponds to region 206. It is a residual effect of overly illuminated area 206 in FIG. 2C. Image FIG. 2E was taken with a slightly smaller collimator opening. Increase 208 due to the detector lag led to significant under-estimation of scatter using a collimator shadow fitting approach.

As discussed below, algorithms disclosed herein can, among other things, ameliorate or even eliminate these charging effects. One way is to measure the effect of illumination in area 206 on the detector while the source 36 is off and prior to obtaining FIG. 2E. This is called "background" B image or data. The background B can then be subtracted or otherwise removed from FIG. 2E using this data to remove the lag effect.

Improved Lag Compensation

In an exemplary variation, one or more background B image is acquired at certain angles of gantry (e.g., gantry 12) rotation while x-ray sources are turned off. In variations, these background B images are used to estimate lag correction accuracy by comparing time-decay response weighted prior images. The background images can also be used to calibrate the lag correction (e.g., pixel-by-pixel). This may enable handling high non-uniformity in patient studies. Background images may also be used to correct MeV scatter. In this case, the background images may be acquired subsequent to turning off an MeV beam. After subsequent background images are acquired, lag correction can be calibrated to handle the MeV beam down scatter more accurately. Scatter correction can be improved by using collimator shadow approaches. Other data-driven scatter correction approaches in RT may be adapted to handle lag from MeV down scatter. Variations described herein include an improved technique for lag correction in CBCT imaging using imaging of background B data.

Background Measurement During Image Acquisition

Figure 3A:
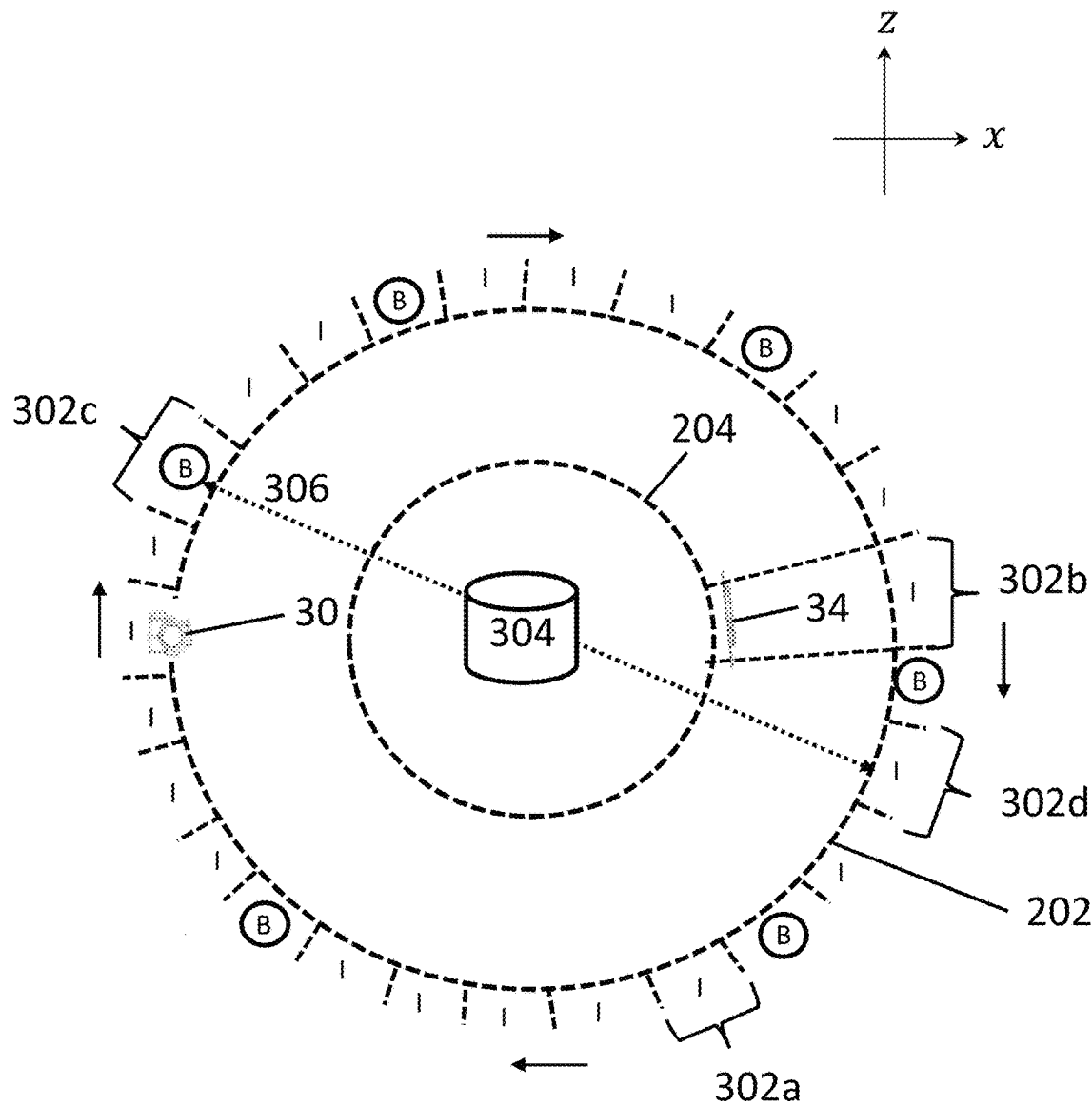
FIG. 3A shows individual angular portions of rotating path 202 where background B or image data I can be measured.

FIG. 3A shows a rotating path 202 for source 30 and rotating path 204 for detector 34 in gantry 12. FIG. 3A divides rotating path 202 into various angular slices (e.g., angular slices 302a-302d). Note that, herein, the term "slice," as in "angular slice," will be used interchangeably with the terms "location" or "position" along one of the paths 202 and 204. It is to be understood that a particular location along the path corresponds to a particular angular slice, and vice versa.

The sizes of angular slices (e.g., 302a and 302b) are merely exemplary. They may include a larger or smaller portion of path 202 than shown in FIG. 3A. In general, there can be a correlation of the slice size to the speed of rotation of the detector 34 and source 30 (i.e., the speed at which source 30 traverses path 202), which may also depend on other factors such as the size of the gantry 12, the energy of the source 30, and the purpose of the scan. Any suitable rotation speed is possible. Exemplary rotational speeds include 1 rpm, 5 rpm, 7 rpm, and 10 rpm, 20 rpm, and 60 rpm. The angular slices need not be uniform, as shown in FIG. 3A.

Each angular slice in FIG. 3A is labeled with an "I" if imaging data is collected in the slice. Angular slices are labeled with a circled "B" if background data is collected in the slice. While the source 30/detector 34 pair is in a location corresponding to an image I slice, source 30 provides imaging radiation. When source 30/detector 34 is in a location corresponding to a background B slice, source 30 is turned off. In order to maximize imaging data I, it may be advantageous to have as few background B slices as possible on path 202. Therefore, strategically determining the locations of background B slides for maximum correction efficacy is important.

FIG. 3A shows exemplary background B positions in the image acquisition. Other positions may be used. Although FIG. 3A shows six background B positions, there may be more or fewer. The exact number may depend on several factors, including rotational speed of the source, resolution of the detector, size of the gantry 12 and length of path 202, etc. In one exemplary variation, there is a background B measurement in 1 out of every 29 angular slices. Background B scans may also be every 7, 15, 30, or 50, or more slices. Some measurements may have background measurements "interleaved" (i.e., every other background on the path: I/B/I/B/I/B . . . ). Generally, the number of background B slices will depend on the angular resolution of the scan. In one variation, 5% of the slices on the paths 204 and 202 can be background B. In another, background can account for 1, 2, 10, 15, 20, or even 30% of the path and/or rotation. However, it is to be understood that there is an inverse correlation between the fraction of the path devoted to imaging I data and background B data. Therefore, there is a trade-off between improved imaging through background B correction and collection of more image I data. For example, the more background B correction that occurs during rotation, the less imaging I data that is available for imaging. Thus, in many cases, it may be preferable to maximize imaging I data between background B correction slices.

In certain instances, the positions B may be arbitrary or random, particularly in the case when the charging and background effects are approximately isotropic. The positions B may be evenly spaced around the circumference of path 202. They may also be placed to coincide follow or preceded to a particular timed event (e.g., the application of treatment or other high energy x-ray radiation from source 20 (FIG. 2A)). One example is positioning background B measurements where there is a large change in x-ray illumination from one frame to the next. This occurs, for example, when a first frame has an image area A fully illuminated by x-rays and the same area A is shadowed from x-rays in the next frame. This maximum difference in illumination between frames creates a maximal probably for a lag effect. Background B measurements of this lag are extremely important for correcting it, since it will have a large impact on the image I data. These possibilities are discussed in more detail below.

Figure 3B:
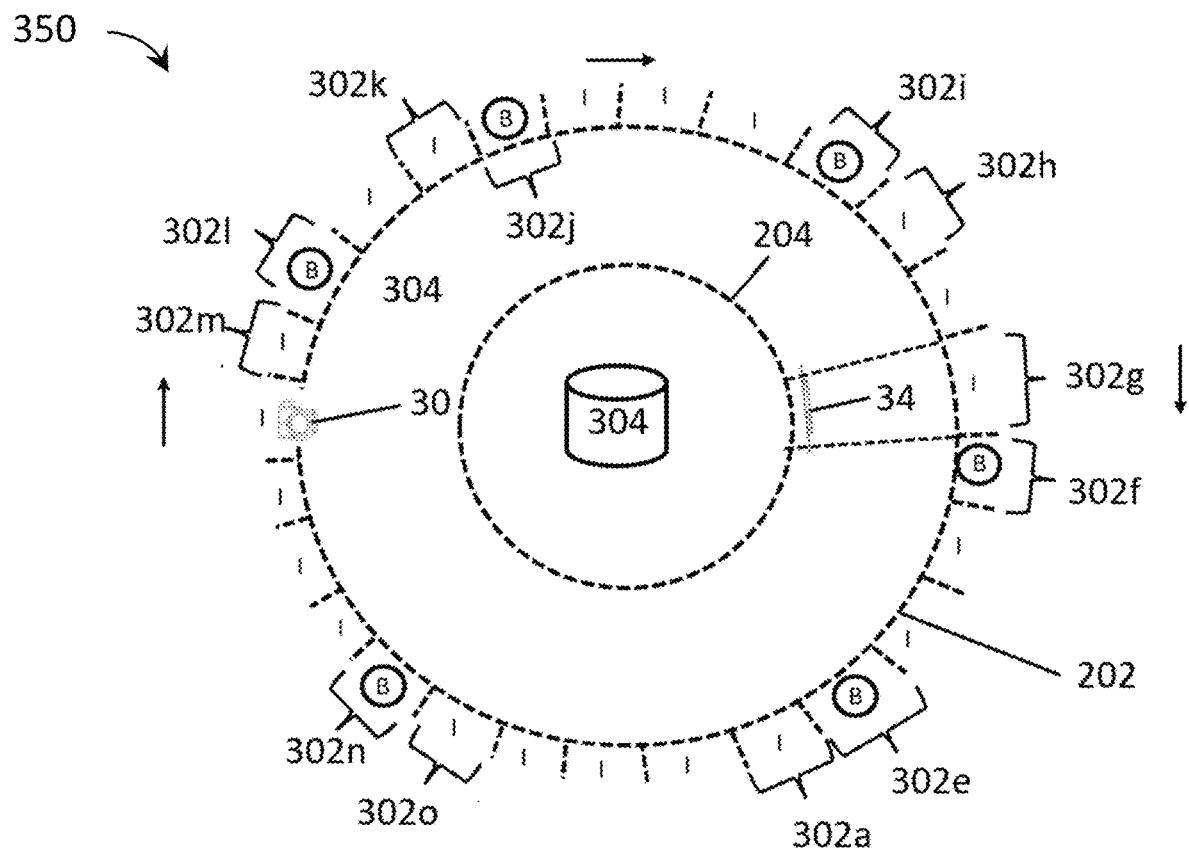
FIG. 3B shows paths 202 for two different, successive rotations 350 and 360 that have staggered background B measurements.

FIG. 3B illustrates the concept of staggering background B angular slice locations in a scan set. It shows a comparison of background B measurement locations in a first angular scan 350 with a second angular scan 360. As mentioned above, data acquisition can include multiple scans (e.g., more than one traversal of detector 34 of path 204). This is done to, for example, average results and increase accuracy. In these multiple scan sets, one important concept is to make sure that the locations of background B data acquisition do not consistently overlap. This overlap results in missing image I data from an angular slice of the object of interest 304. It will result in a final tomographic image missing this data and, therefore, being incomplete.

FIG. 3B shows staggering background B locations to prevent this overlap. The first scan 350 has background locations B that are identical to those in FIG. 3A. Specifically, in first scan 350, background B is measured at locations 302e, 302f, 302i, 302j, 302l, and 302n. Background in the second scan 360 is deliberately measured at different locations 302a, 302g, 302h, 302k, 302m, and 302o. Although the example case of FIG. 3B shows the background B measurements repositioned to neighboring slices between the first 350 and second 360 scans, this is merely exemplary. Any new configuration of background locations is possible, so long as overlap of background B locations with the previous scan is lowered or minimized.

Determining Background B Measurement Positions

Different methods can be used to determine which angular slices measure background B and image I data. One method is to use a planning CT image taken prior to treatment and/or imaging. As used herein, "planning CT" images are typically high quality, high contrast resolution images that provide fine features and contours of organs for dose planning. They can be used to set contrast and other features of the x-ray beam and resultant imagery. From the planning CT, projection data in CBCT acquisition can be simulated or predicted. Any suitable algorithm can be developed to determine distribution of background B locations within path 202 based on the planning CT. Placement of background B locations may be optimized for maximum corrective effect and/or minimal image I data forfeit. Placement may also take into account other considerations than maximizing corrective effect (e.g., regions of interest in the object 304, timing of the application of various radiation sources, computational time, power usage, significantly, large variations in signal level on a pixel from one view to the next, or over some span of views, etc.).

Another consideration for placement of background B measurement is avoiding measuring background B for conjugate angles (e.g., at both slices 302c and 302d). Source 30 illuminates the same portion of object 304 at conjugate angles (e.g., 302c and 302d, as shown by illumination path 306). Therefore, it is advantageous to have imaging I data acquisition for at least one of the conjugates so that any reconstructed 3D image may include at least one image I data from the corresponding portion of object 304. If background B images were acquired at both conjugates, e.g., 302c and 302d, there would be no image I data for this portion of object 304.

Other parameters may be varied in order to optimize or improve background B measurement and correction, or for other purposes. Although FIG. 3A appears to show paths 202 and 204 as circular, they can and likely do have other shapes such as helical or approximately helical. This is because the patient or object of interest 304 is typically moving in a direction in or out of the page (with respect to FIG. 3A) while the scan is conducted. Paths 202 and 204 may also be elliptical or have still other shapes. Many of the considerations regarding placement of background B measurements discussed in the context of the circular paths shown in FIG. 3A will apply to these other shaped paths. There may also be additional considerations. For example, in the case of helical paths, the pitch (or other parameters) of the helix may be varied to improve background B measurement and/or correction.

Simulated x-ray projection data (e.g., simulating the projection of x-rays from source 30 through object 204 and detected by detector 34) can be used to determine at the angular slices a background B acquisition will benefit the lag correction the most. The determination can be made, for example, by measuring background B where detector 34 receives the highest radiation levels. As discussed above, background measurements B can also be timed with respect to the application of certain types of radiation (e.g., MeV therapeutic radiation). Angular slices subsequent to application of high energy x-rays can have lag or charging effects. Therefore, it will likely be advantageous to collect background B near them in order to compensate for the background, as described below. They may also be timed based on the severity of changes in object 304 illumination with time. Criteria for the distribution of background B measuring angular slices around path 202 can also include angles with large change of detected x-ray intensity. These changes can be due to large contrast change in the patient, or orientational change (such as at anterior/posterior, or AP, and left/right, or L/R).

Other possible sources for input to the algorithms discussed herein include 2D survey images taken at a single angle over a certain length of the patient or object 304. The 2D survey images may include orthogonal angles (e.g., anterior/posterior (AP), left/right (LR)). They can be used to determine at which angles to acquire the background images for lag correction. Any other suitable image may be used to determine background measurement B locations. Suitable image sources include image models of a patient or object of interest, images taken via other CT/x-ray devices, and/or optical images, etc. Images and/or prior data may be used to generate a patient-specific or object-specific lag model. The patient-specific model, for example, may incorporate features of a CT scan of the patient either from the same device measuring background, or from earlier images.

In addition or alternatively, any of the algorithms described herein may identify an angle group for background B measurement predetermined by means other than image analysis. For example, the algorithms on using general patient atlas, patient models (general or phenotypical), phantom models, other mathematical models, and/or physical models. A "patient atlas," as used herein, denotes a mapping of the patient contours observed in x-ray imaging. Patient atlases may be obtained from a variety of sources including a patient atlas developed based on a large collection of patient images acquired on the apparatus performing the methods disclosed herein.

The algorithms described herein may determine angular slices for measuring background B during acquisition. Specifically, after certain angles are acquired, the algorithm analyzes the images already acquired and determines if a background image should be acquired.

Angles for background B measurements in the detection data can be identified in data by adding a tag in header, or other data files. These designations can be used to separate background B data from image I data. The designations can be automatically detected using various algorithms. Suitable detection algorithms include those that produce total counts in each view. Angles for background B can be much lower than those of neighboring angles with beam on. For example, the signal in a background image with x-ray off could be two orders of magnitude lower than the neighboring angles with x-ray on in the region with direct x-ray illumination or near the boundary of patient body.

Background B data may be obtained during patient scans for detector lag correction. For example, background B data may be taken during an acquisition sequence pre-determined prior to a scan or calculated during the scan (e.g., on-the-fly). In addition, algorithms may use measured background B information for a patient to automatically generate a set of advantageous or optimal background B measurement positions for that patient. In this and other algorithms described herein, an interpolation may be used. The total number of background B data acquisitions may be small compared to the total number of projection views (i.e., views B and I associated with the angular slices along path 202 in FIG. 3AB). In particular, this may facilitate accurate image reconstruction. This can be performed while the background projection images can be used to improve the lag correction.

The angular distribution of background B measurements along path 204 may be deliberately changed with time, particularly for different image scans. In one variation, two or more full rotations of source 30 are used to generate image I data for one 3D reconstruction. The locations of the background B measurements in the two rotations may be deliberately made different so that every possible angle along path 304 has at least one image I data scan. In other words, the algorithm can ensure that angles or positions along path 204 assigned to background B measurements in the first rotation may be assigned differently for image I measurements in the second, and vice versa (e.g., as shown in FIG. 3B). It is to be understood that the discussion of two scans here is merely exemplary. This technique may be employed with any suitable number of scans. It may also be employed for helical scans where background B data collection locations are deliberately changed between scans. In any case, the reconstruction can estimate data for these angles from data from neighboring angles (e.g., interpolation) and the corresponding angles in subsequent or previous rotations.

The angular distribution of background B measurements can also be determined based on live data during imaging. A model describing the dependence of angular distribution of background B can be based on a change in signal measured at each pixel, for example. The model may impose a background B measurement when that change increases beyond a certain threshold.

Detection and Correction of Image I Data Using Background B

Detectors (e.g., detectors 24 and 34, which may be flat panel detectors), x-ray tube (not shown), and system control (e.g., controller 60) can be synchronized to acquire background data B, at which the x-ray source (e.g., sources 20 and 30) can be turned off. In an RT scenario when an MeV beam (e.g., from source 20) is turned on, information regarding detected radiation may be passed to a CT acquisition control (e.g., element 60, FIG. 2A) to initiate a background B acquisition after the MeV beam is turned off. Alternatively, an algorithm can detect if the MeV beam is turned on. In that case, the image impacted by the MeV beam will be tagged. A signal can be generated to trigger the CBCT system to acquire one or multiple background images. In the case when the MeV beam is turned on during CBCT scan, the angle group predetermined for background images may be adjusted accordingly. An algorithm may be developed to perform this adjustment.

One advantageous use of background B measurements is via linear interpolation. For example, a first background B measurement can be performed just prior to an image I acquisition. A second background B measurement can be performed just after the image I acquisition. The two background measurements adjacent in time and angle to the image I measurement can then be linearly interpolated to create a composite background error image with the features of both measurements. This composite background image can then be used to correct the image I data with higher accuracy than by using one or the other background image.

Background B correction may use background measurements B in real time. It may be used to update and improve a background correction approach based on time-decay models. For example, the time-decay modeling lag correction being used to correct data may be recalibrated with new information obtained by ongoing or new background B measurements. As with other algorithms described herein, this may be accomplished using interpolation methods, among others. Background B information from multiple background measurements may be combined to provide a correction. This may be particularly advantageous where one of the scans provides background B information relating to a temporary condition (e.g., where an x-ray source for therapeutic radiation 20 is switched on or just switched off).

In variations, lag correction may be updated with background information. In lag correction, images from certain angles are weighted by using a measured time-decay response of the detector used to detect them. The weighted images can then be subtracted from a current image to correct that image. The time-decay response is most typically determined based on prior detector measurements. The time interval in which the previous images are used for lag correction is most typically empirically determined based on the time-decay response. Accuracy of the correction depends on these parameters.

Any of the background measurements described herein may be used in conjunction with a time-delay correction. For example, the time-delay correction may be re-calibrated periodically based on background images. It may be, for example, recalibrated based on every background image, based on a combination of background images, or based on an average of background images. It may include more than one decay term.

Reconstruction of corrected image I data may be performed using any suitable conventional analytical reconstruction. Typically, such algorithms prefer or mandate that the image I data be acquired from evenly distributed positions along path 204. Such reconstruction schemes may be modified to accommodate irregular background imaging along path 204 so that the background B measurement positions can be configured and/or optimized. An image reconstruction algorithm can be modified to compensate for the lack of data at angle positions where background B data is obtained. Compensation can be accomplished by any suitable method. One example is to use a view-by-view analytical recon and/or iterative recon. Such techniques may minimize the impact of the subset of angles used only for background B data collection.

Reconstruction may include data from multiple scans and rotations, as discussed above. Image reconstruction algorithms may include projection angular sampling. In particular, azimuth angular positions of the background B images of the current rotation differ from those of other rotations, particularly rotations that come directly before and after the current rotation. In this and other cases it may be preferable to interleave, in some cases maximally interleave, the background B measurements from rotation to rotation. This consideration may use data redundancy and helical pitch, as discussed above.

More conventional reconstruction algorithms may be modified in this approach. For example, conventional algorithms may require evenly (angularly) spaced images. This requirement may be relaxed and modified to accommodate background B images spaced according to any of the schemes, algorithms, or examples described herein. The modifications may account for uneven spacing between background collection angles and uneven spacing between image collection angles. It may consider a difference between azimuth angular positions of background images different rotations of source 30. In some variations, azimuth angular positions of one rotation may be interleaved with azimuth angular positions of another rotation.

Exemplary Implementation of Algorithm

Figure 4A:
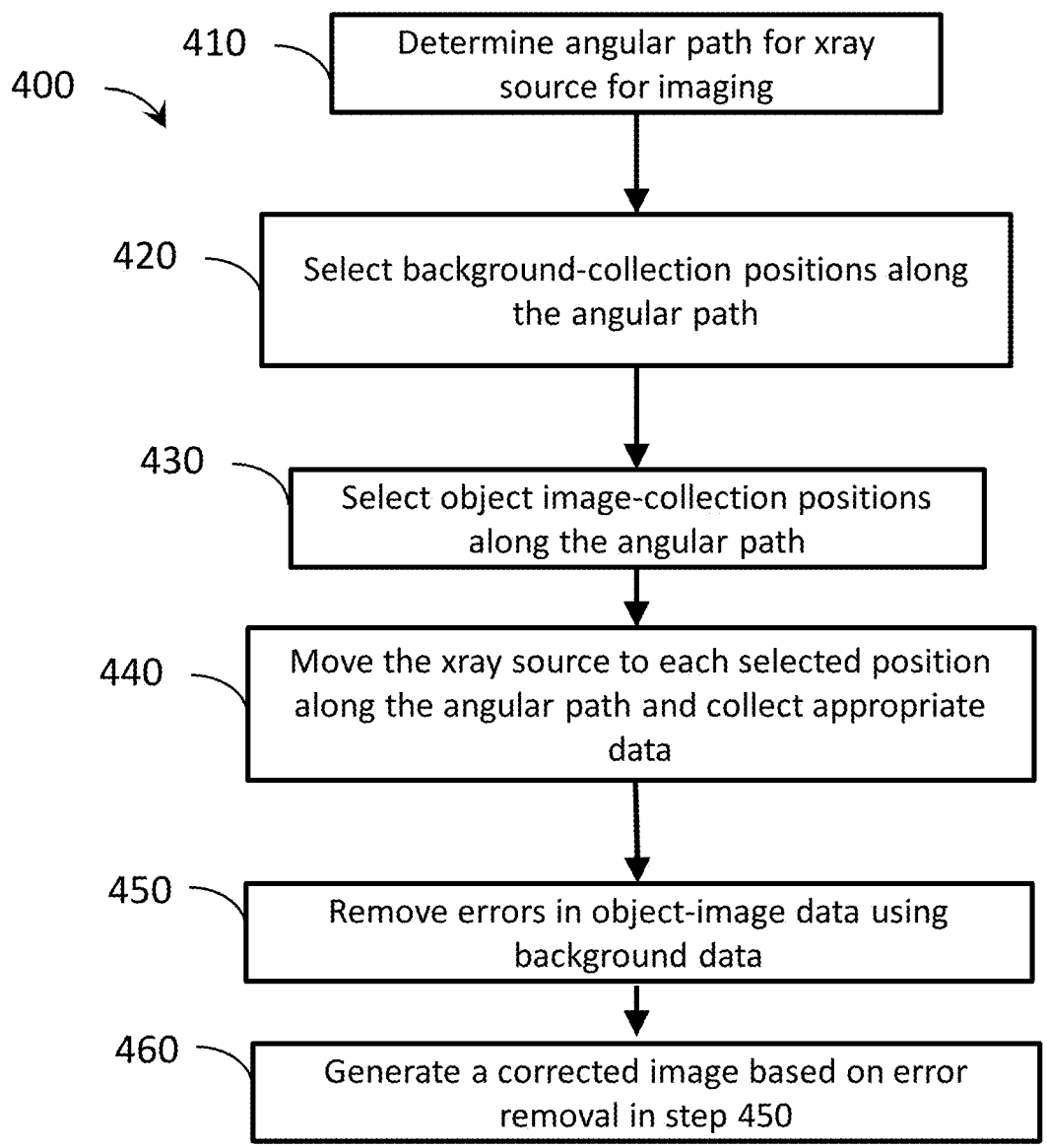
FIG. 4A is a flowchart showing a method 400 that can be implemented according to the present disclosure.
Figure 4B:
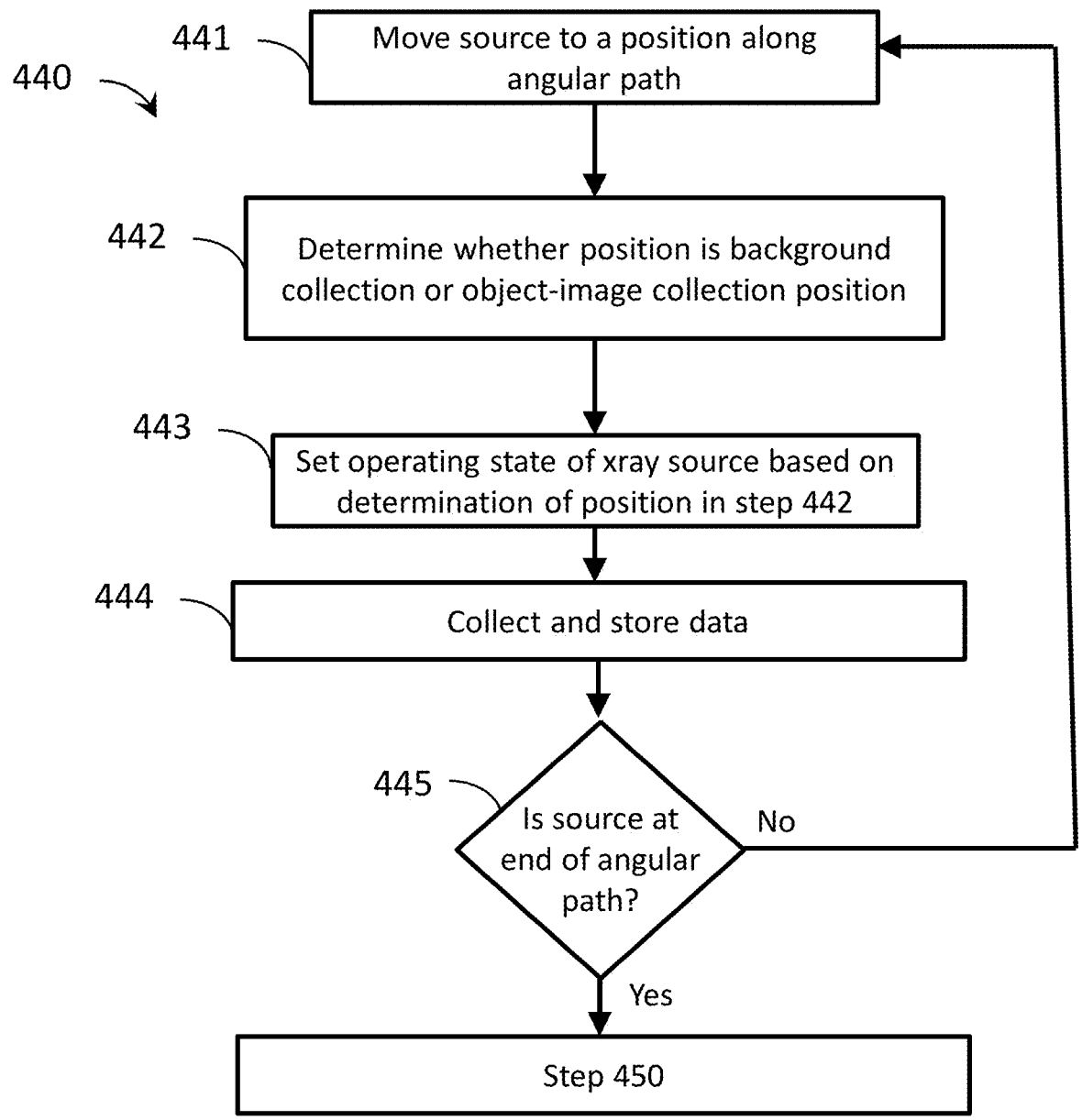
FIG. 4B is detail of step 440 in method 400.

FIGS. 4A and 4B show an exemplary algorithm 400 that may implement any of the steps and techniques described herein to correct image lag or ghosting (FIGS. 2B-2F). It is to be understood that algorithm 400 is general and may incorporate any variation of any method or algorithm discussed above. Although specific steps are shown, no one specific step is required. Additional steps may be added to algorithm 400 and still be within the context of the present disclosure. Algorithm 440 may be performed with any suitable apparatus, including all apparatuses described herein (e.g., apparatus 10 in FIG. 1). It may be performed with apparatuses that have only imaging capability. It may also be performed with apparatuses that operate in an RT configuration.

Figure 3B:
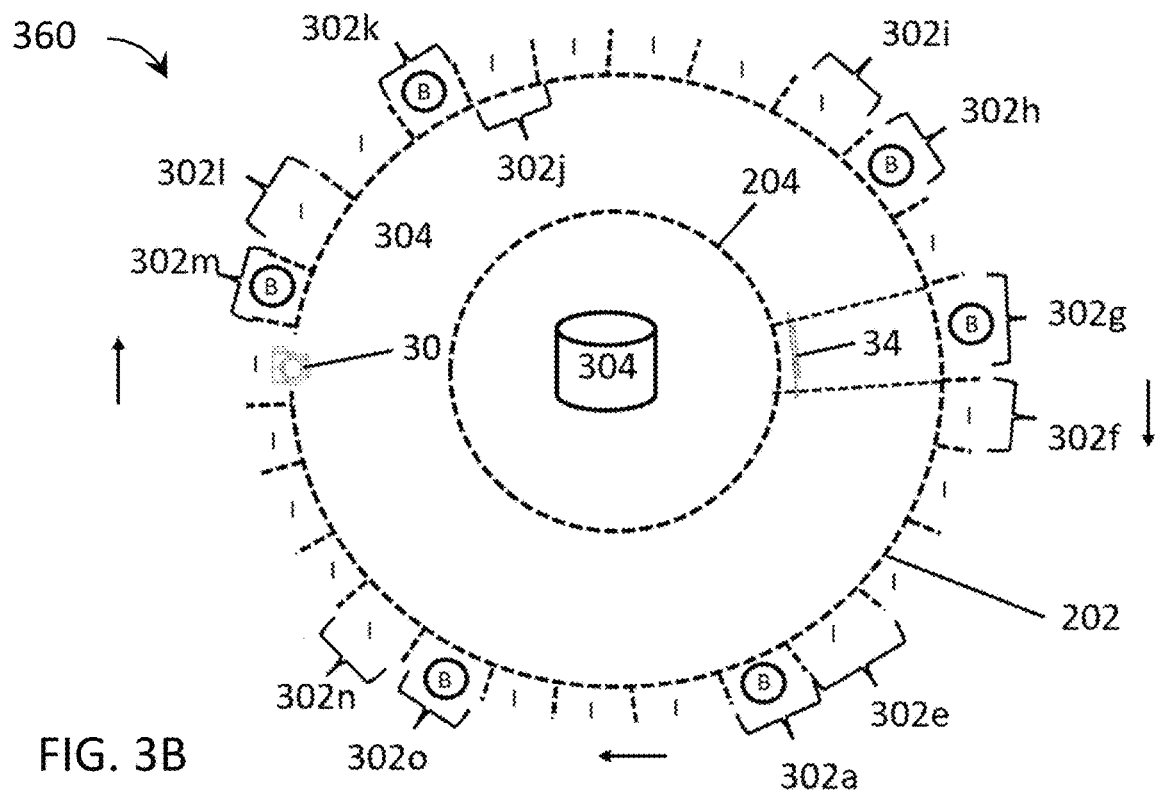

In step 410, algorithm 400 determines an angular path for the x-ray source to traverse during imaging. This path can be pre-determined by the physical configuration of the imaging device (e.g., as path 202 is for source 30 shown in FIGS. 2B and 3). In some variations the path may be changed by algorithm 400. For example, if the path is helical, the pitch of the helix may be altered to improve, for example, background B measurements. Any other suitable path determinations or alterations are possible.

In step 420, background B measurement positions may be selected along the path identified in step 410. Any suitable background B measurement positions may be selected according to any of the considerations described herein. In many cases, it may be advantageous to minimize or keep substantially low the number of background B measurement positions in order to maximize image I information collected. In others, as discussed above, it may be advantageous to increase background B measurements in order to capture a certain temporal phenomenon (e.g., the onset or switching off of an x-ray source). As discussed above, background B collection locations may be selected for more than one rotation.

As discussed above, background B position may be selected via algorithm. The algorithm may make the selection based on any suitable number of inputs, including current and previous images. Any other input or consideration may be made to select background B locations in this step. Although FIG. 4A shows step 420 occurring before data acquisition (step 440), step 420 is not limited to this ordering. Step 420 may be performed before or during step 440. Any suitable algorithm may perform this step including machine learning algorithms such as artificial neural networks and decision trees. Other numerical regression techniques may also be used.

In step 430, the object-image collection positions are selected. In many cases, this step will be accomplished effectively by the selection of background B measurement positions in step 420 because only background B and image I measurement positions are possible. In others, there may be positions that correspond to neither a background B or image I measurement. For example, it may be advantageous to take no data or to take and discard data when certain transients that cannot effectively be compensated for via background B subtraction are affecting x-ray detection signal. These may include transients that happen too quickly for an effective background B measurement.

In step 440, the x-ray source (e.g., source 30) is moved along the path selected in step 410 in order to collect images. The collected images will be both background B data and image I data. The positions at which these data are collected will be according to step 420.

In step 450, errors (e.g., lag or ghosting effects, as shown in FIGS. 2B-2F) in image data I may be corrected using background data B. This correction may be performed by any of the methods described herein. One example is simply subtracting a background B data image from an image I. Others include interpolation techniques, e.g., interpolating two or more background images, both in combination with subtraction and not. Still other techniques may include selectively altering pixels in the image (e.g., by convolving) based on issues identified via the background image. Any suitable algorithm may perform this step, or it may be performed manually. Suitable algorithms include machine learning algorithms such as artificial neural networks and decision trees. Other numerical regression techniques may also be used.

In step 460, the results of the correction in step 450 are used to generate a corrected image. This could be an individual 2D image of a particular scan. It could also be a 3D tomographic reconstruction including many such 2D images. The corrected image may be used for any suitable purpose, including patient diagnosis and treatment. It may also be used to help generate background B measurement positions and or to inform any other aspect of algorithm 400 described above.

FIG. 4B shows detail of the image acquisition step 440 in algorithm 400. Acquisition step 440 may be performed iteratively over one or more movements of the x-ray source. Step 440 is generally performed until a complete set of imaging I data is acquired. Whether a set is "complete" is relative to the task at hand. It may include one or more images I corresponding to one or more rotations. Typically, the rotations traverse the entire path identified in step 410. However, it is to be understood that this need not be the case for every implementation of step 440.

In step 441, the source (e.g., source 30) is move along the angular path to a particular position. In step 442, algorithm 400 determines whether the current position corresponds to background B or image I collection. As discussed above, there may also be other options (e.g., some positions may be flagged for no data acquisition in other to allow transient dissipation). The determination of the type of data to acquire may be based on use of any algorithm or considerations discussed above. Once the data type is selected, the algorithm sets an operating state of the x-ray source in step 443 according to the data type selection. If the data to be acquired is background B data, the source will either be switched off or, if it is already off, or will remain powered down. If the data to be acquired is image I data, the source will be either powered up, if not already powered, or kept on. Once the operating state of the source has been implemented, data of the appropriate type will be collected and stored in step 444. The algorithm 400 may wait to collect data until transients caused by switching the operating state of the source have dissipated. Once the data is collected, algorithm 400 will query whether the source has reached the end of the path at step 445. If so, algorithm 400 will proceed to step 450 (FIG. 4A) to remove errors in the collected data. If not, algorithm 400 will return to step 441 to move the source to a new position. Algorithm 400 will repeat this process until it has reached the end of the path designated in step 410.

When the above apparatus and methods are used in the projection domain, it can be applied on each projection view, where each projection view is a planar image. Various embodiments can utilize different scan geometries, detector positioning (including offset detectors), and/or beamformer window shapes.

As is discussed above, aspects of the disclosed technology can be utilized in a radiotherapy device and methods that make use of multimodal radiation sources, including integrated low energy (e.g., keV) and high energy (e.g., MeV) sources for use in conjunction with or as part of IGRT. In accordance with one embodiment, the image acquisition methodology can include or otherwise makes use of a helical source trajectory (e.g., a continuous source rotation about a central axis together with longitudinal movement of a patient support through a gantry bore) or a circular scan, together with fast slip ring rotation, for example, to provide keV CT imaging on a radiation therapy delivery platform.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An imaging system comprising:
a first x-ray source configured to:
produce first x-ray photons in a first energy range suitable for imaging;
project the first x-ray photons onto an area designated for imaging;

a rotatable gantry configured to rotate the first x-ray source such that the first x-ray source traverses an angular path; and a data processor having an analytical portion configured to:
- collect first data relating to the transmission of the first x-ray photons through the area designated for imaging at a set of image-collection angles along the angular path;
- collect background data at a set of background-collection angles along the angular path, wherein the system acquires more than one image of the designated area for imaging between background angles;
- remove errors in the first data using the background data; and
- generate a corrected image based on the removal of errors in the first data.

2. The system of claim 1, wherein the analytical portion determines the set of background-collection angles at least in part by determining a minimum number of background measurements.

3. The system of claim 2, wherein the analytical portion determines the set of background-collection angles at least in part by maximizing the set of image collection angles between the background-collection angles.

4. The system of claim 1, wherein removing errors from the first data using the background data comprises:
- weighting images using a measured time-decay response of an x-ray detector; and
- subtracting the weighted images from the first data.

5. The system of claim 4, wherein the analytical portion recalibrates the time-decay response based on the background data.

6. The system of claim 5, wherein recalibrating the time-decay response is based on more than one background image and includes more than one decay term.

7. The system of claim 1, wherein removing errors in the first data using the background data comprises interpolating background images.

8. The system of claim 1, wherein the system includes a Cone-Beam Computed Tomography (CBCT) system.

9. The system of claim 1, further comprising:
a second x-ray source configured to:
- produce second x-ray photons in a second energy range different in energy than the first energy range;
- project the second x-ray photons onto an area designated for imaging; and
wherein the analytical portion is configured to at least one of:
- combine data derived from the first and second x-ray photons;
- interleave application of the first and second x-ray sources; and
- concurrently operate the first and second x-ray sources.

10. The system of claim 1, wherein the set of background-collection angles are evenly distributed along the angular path.

11. The system of claim 1, wherein the set of background-collection angles are distributed at pre-determined angles along the angular path.

12. The system of claim 1, wherein the set of background-collection angles are determined via at least one of analyzing a planning computed tomography (CT) image, analyzing a previously available CT image, analyzing a CT 2D survey image, analyzing an image in orthogonal angles, analyzing a patient atlas, analyzing data during acquisition.

13. The system of claim 1, wherein the set of background-collection angles are determined using at least one of a patient geometry, an acquisition protocol, and a projection angle relative to patient orientation.

14. The system of claim 1, wherein the analytical portion determines the set of background-collection angles via an algorithm.

15. The system of claim 14, wherein the algorithm determines the set of background collection angles based on improving accuracy of CBCT reconstruction.

16. The system of claim 14, wherein the algorithm excludes conjugate angles from the set of background collection angles.

17. The system of claim 14, wherein the algorithm selects background collection angles based at least in part on the use of MeV radiation.

18. The system of claim 14, wherein the algorithm selects background collection angles to improve at least one of lag correction and data-driven scatter correction.

19. The system of claim 14, wherein the removing errors in the first data using the background data comprises:
- collecting background data at a first angle along the angular path;
- collecting the first data at a range of angles along the angular path;
- collecting background data at a second angle along the angular path, the second angle positioned such that the range of angles is between the first and second angles;
- generating an error image by interpolating the background data collected at the first and third angles; and
- removing errors in the first data using the error image.

20. The system of claim 14, wherein the algorithm generates a first set of background collection angles for a first scan and a second set of background collection angles for a second scan, and the first and second sets are different.

21. The system of claim 20, wherein the first and second sets do not overlap.

22. The system of claim 14, wherein the angular path is helical.

23. The system of claim 22, wherein the algorithm determines the background collection angles at least in part based on a pitch size of the helix.

24. The system of claim 14, wherein the algorithm determines the background collection angles at least in part based on improving the accuracy of a 3D image reconstruction using the image data.

25. The system of claim 14, wherein an image reconstruction selects a different set of background collection angles for different rotations of the first source.

26. The system of claim 1, wherein the analytical portion synchronizes an x-ray control, a flat panel detector readout, and a CT scan control so that the flat panel detector readout will provide background data when the first x-ray source is powered off.

27. The system of claim 26, wherein a movement of the first x-ray source along the angular path is uninterrupted while the x-ray source is powered off.

28. The system of claim 1, wherein the analytical portion is further configured to generate a 3D reconstruction by modifying a reconstruction algorithm based on the background collection angles.

29. The system of claim 28, wherein modification accounts for an uneven spacing between background collection angles and an uneven spacing between image collection angles.

30. The system of claim 28, wherein modification considers a difference between azimuth angular positions of background images in a first rotation of the first x-ray source and azimuth angular positions of background images in a second rotation of the first x-ray source.

31. The system of claim 30, wherein the azimuth angular positions of the first rotation are interleaved with the azimuth angular positions of the second rotation.

32. An imaging system comprising:
an x-ray source configured to:
   produce x-ray photons in an energy range suitable for imaging;
   project the x-ray photons onto an area designated for imaging;
a rotatable gantry configured to rotate the x-ray source such that the first x-ray source traverses an angular path; and
a data processor having an analytical portion configured to:
   collect background data at a first angle along the angular path;
   collect image data relating to the transmission of the x-ray photons through the area designated for imaging over a range of angles along the angular path;
   collect background data at a second angle along the angular path, the second angle positioned such that the range of angles is between the first and second angles;
   generate a corrected image by removing errors in the image data using an interpolation of the background data collected at the first and second angles.

33. The system of claim 32, wherein the analytical portion determines the first angle, the second angle, and the range of angles at least in part by determining a minimum number of background measurements for accurate background estimation.

34. The system of claim 33, wherein the analytical portion determines the first angle, the second angle, and the range of angles at least in part by maximizing at least one of a total number of images of the designated area for imaging and a number of images of the designated area for imaging taken between each of the background-collection angles.

35. The system of claim 32, wherein removing errors from the image data comprises:
   weighting images using a measured time-day response of an x-ray detector; and
   subtracting the weighted images from the first data.

36. The system of claim 35, wherein the analytical portion recalibrates the time-decay response based on the background data.

37. A method of an operating an imaging system comprising:
   producing first x-ray photons in a first energy range suitable for imaging;
   projecting the first x-ray photons onto an area designated for imaging;
   rotating the first x-ray source such that the first x-ray source traverses an angular path;
   collecting first data relating to the transmission of the first x-ray photons through the area designated for imaging at a set of image-collection angles along the angular path;
   collecting background data at a set of background-collection angles along the angular path, wherein the system acquires more than one image of the designated area for imaging between background angles;
   removing errors in the first data using the background data; and
   generating a corrected image based on the removal of errors in the first data.

38. An imaging system comprising:
a first x-ray source configured to:
   produce first x-ray photons in a first energy range suitable for imaging;
   project the first x-ray photons onto an area designated for imaging;
a rotatable gantry configured to rotate the first x-ray source such that the first x-ray source traverses an angular path; and
a data processor having an analytical portion configured to:
   collect first data relating to the transmission of the first x-ray photons through the area designated for imaging at a set of image-collection angles along the angular path;
   collect background data at a background-collection angle along the angular path;
   remove errors in the first data using the background data; and
   generate a corrected image based on the removal of errors in the first data.

* * * * *